US006341152B1

(12) United States Patent
Sugihara

(10) Patent No.: US 6,341,152 B1
(45) Date of Patent: Jan. 22, 2002

(54) X-RAY COMPUTERIZED TOMOGRAPHY APPARATUS

(75) Inventor: Naoki Sugihara, Tokyo (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/393,270

(22) Filed: Sep. 10, 1999

(30) Foreign Application Priority Data

Oct. 2, 1998 (JP) .......................................... 10-281622

(51) Int. Cl.[7] .................................................. G21K 5/08
(52) U.S. Cl. .............................................. 378/4; 378/20
(58) Field of Search ................................. 378/4, 20, 41

(56) References Cited

U.S. PATENT DOCUMENTS

| | | | |
|---|---|---|---|
| 5,513,237 A | | 4/1996 | Nobuta et al. |
| 5,566,218 A | | 10/1996 | Nobuta et al. |
| 5,608,772 A | * | 3/1997 | Nobuta et al. |
| 5,627,868 A | | 5/1997 | Nobuta et al. |
| 5,740,222 A | | 4/1998 | Fujita et al. |
| 5,748,696 A | | 5/1998 | Fujita et al. |
| 5,848,126 A | | 12/1998 | Fujita et al. |
| 6,081,577 A | * | 6/2000 | Webber ........................ 378/23 |

* cited by examiner

*Primary Examiner*—David V. Bruce
*Assistant Examiner*—Pamela R. Hobden
(74) *Attorney, Agent, or Firm*—Oblon, Spivak, McClelland, Maier & Neustadt, P.C.

(57) ABSTRACT

There is disclosed an X-ray computerized tomography apparatus capable of accurately and promptly carrying out a navigation of an operation, by real-time reconstructing and displaying an image of a slice in which an object such as an insertion object inside a subject exists. This X-ray computerized tomography apparatus is structured to include: an X-ray detection unit for detecting transmission X-rays from a plurality of directions Irradiated from an X-ray beam generation source and transmitted through a subject, a data acquisition unit for acquiring transmission data according to the transmission X-rays detected by the X-ray detection unit, an object position detection unit for detecting a position of an object inside the subject, according to a part of the transmission data, a reconstructing range determining unit for determining a slice to be image-reconstructed, according to the position detected by the object position detection unit, and an image reconstruction unit for reconstructing a tomographic image of a slice in which the object exists, according to a transmission data acquired by the data acquisition unit, the transmission data being acquired in the slice. Thus, the X-ray computerized tomography apparatus directly detects the position of the object from the acquired transmission data, and controls the image reconstruction, display or scanning, based on the detected position.

47 Claims, 21 Drawing Sheets

SLICE (BODY AXIS) DIRECTION

NUMBER OF ROWS

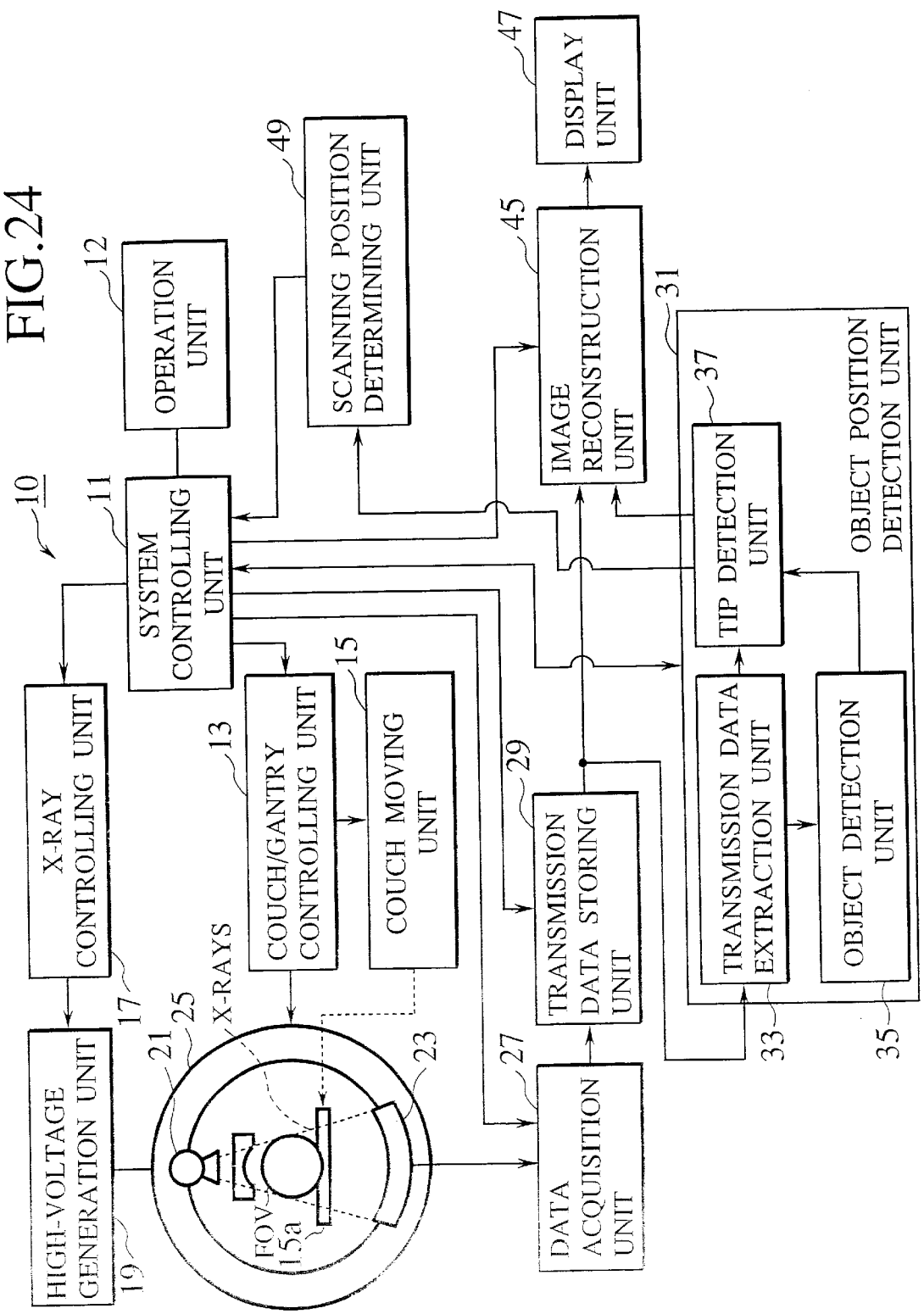

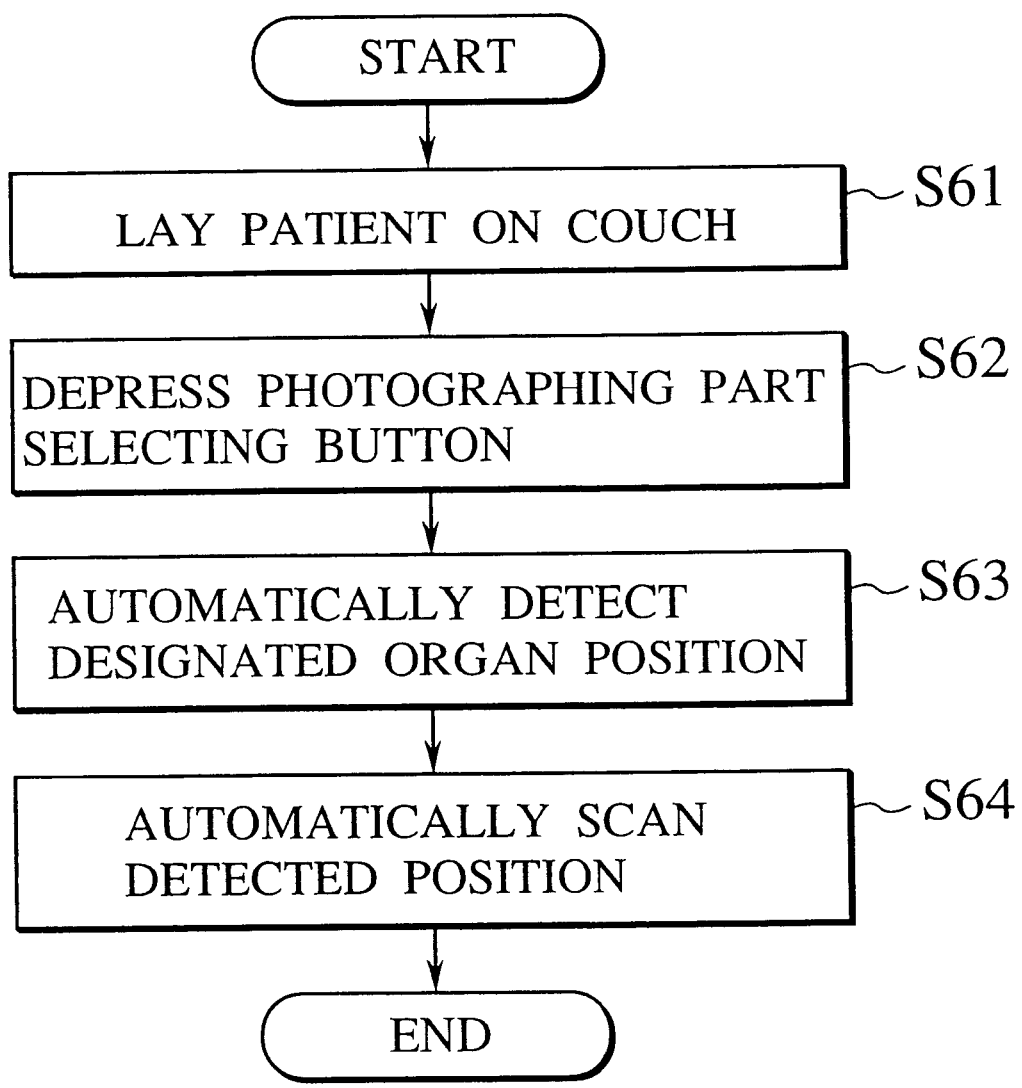

X-RAY COMPUTERIZED TOMOGRAPHY APPARATUS

BACKGROUND OF THE INVENTION

1. Field of the Invention

The present invention relates to an X-ray computerized tomography apparatus. The present invention relates, more particularly, to a technique for achieving a prompt and real-time display of a display image of a desired arbitrary target object within a subject by easily detecting a position of the object at a high speed, and for improving the efficiency of the operation in a navigation of an operation or the like, for example.

2. Description of the Background

In the application field of an X-ray computerized tomography apparatus, there has been known so-called a CT fluoroscopy or a real-time CT (hereinafter referred as a CT fluoroscope) utilizing a real-time reconstructing method for reconstructing and displaying acquired projection data in real time. By utilizing this CT fluoroscopy technique, it is possible to carry out a navigation of an operation including a biopsy for collecting an organization of a target object such as a tumor from a subject, and an insertion of a catheter In this case, a photographing of a tomographic image of the subject is carried out first, by using an X-ray computerized tomography apparatus. Then, an insertion object such as a catheter or a puncture needle is inserted into the subject, and this insertion object is reached to a target object like a tumor existing inside the subject, while confirming the tomographic image displayed on the screen.

As a conventional X-ray computerized tomography apparatus for carrying out an operation support, there has been known an operation supporting system disclosed in U.S. patent application Ser. No. 5,848,126, "Radiation Computed Tomography Apparatus". According to this operation supporting system, an image reconstructing of a subject is carried out after scanning the subject, to generate image data consisting of data of a plurality of slices. Then, a position of an insertion object is detected from this image data, and a tomographic image including a slice having a tip of the insertion object is displayed on the screen.

The above-described conventional art, however, has the following problems.

FIG. 1 shows a procedure of reaching a target object inside a subject by a biopsy or the like according to the conventional art. At first, an operator inserts a puncture needle into the subject while watching a display image (step S101). In this case, according to the image display based on the conventional X-ray computerized tomography apparatus, as the insertion object is inserted into the subject, the tip of the insertion object is deviated from the image of a slice displayed, so that the tip (probe tip) of the insertion object is lost from the view field. When the insertion object such as puncture needle tip is deviated from the image (step S102Y), a doctor (or the operator) moves a gantry or a couch to change a slice to be displayed on the screen while observing the image (step S103). Until the image of the puncture needle tip is confirmed (step S104Y), the move of the gantry or the couch in step S103 has to be repeated, and then the puncture needle reaches a target position (step S105Y), these processes have to be repeated. In other words, the operator always needs to move the gantry or the couch in search of the tip of the insertion object, which work has required a considerably large word load.

Further, according to the above-described operation supporting system, it has been necessary to provide an insertion object supporting member having a position detecting function (sensor function), for detecting the tip of the insertion object. The provision of the insertion object supporting member for the insertion object has made it difficult to carry out a free operation of the insertion object.

Furthermore, according to the above-described operation supporting system, after the subject has been scanned, image reconstructing is carried out for the data acquired by the scanning, to thereby prepare image data. The insertion object is detected from this reconstructed image data. However, the series of the Image reconstructing and the image data preparation processing takes long hours. Therefore, it has not been possible to detect and display the insertion object in real time.

On the other hand, the photographing of a target organ in the subject has required the following complex operation.

FIG. 2 shows a procedure for photographing a target organ inside a subject.

At first, the operator lays a patient on the couch (step S601), and photographs a whole scanogram of this patient (the subject) (step S602). Next, the operator determines a scan position for photographing the target organ on the image (step S603) while observing the photographed scanogram image. The operator operates to start the scanning (step S604), and obtains a tomographic image of the target organ.

The series of the above procedure takes long hours, and the operation required therefor has been complex

SUMMARY OF THE INVENTION

The present invention has been made to overcome the above-described problems of the conventional art. It is an object of the present invention to provide an X-ray computerized tomography apparatus capable of real-time reconstructing and displaying an image of a slice in which a target object such as an insertion object inside a subject exists so as to accurately and promptly carry out a navigation of an operation.

It is another object of the present invention to provide an x-ray computerized tomography apparatus capable of decreasing an unnecessary exposure of a subject to X-rays, by real-time acquiring transmission data of only a slice in which a target object such as an insertion object inside the subject exists.

Further, it is still another object of the present invention to provide an X-ray computerized tomography apparatus capable of improving the operation efficiency of the photographing of a target organ inside a subject.

In order to achieve the above objects, a first feature of the present invention resides in directly detecting a position of an object inside a subject from transmission data acquired (i.e., projection data). Based on the information of the detected position, it is possible to determine a range in which an image should be reconstructed, a range in which an image should be displayed (visualized), or a range in which a subject should be scanned, and to carry out a prompt processing in a necessary range.

Further, a second feature of the present invention resides in displaying arbitrary data among acquired transmission data, together with a display image of a reconstructed image. By displaying this transmission data, It is possible to easily understand in real time the progress state of an insertion object three-dimensionally.

According to one aspect of the present invention, there is provided, as shown in FIG. 3, an X-ray computerized tomography apparatus, comprising: an X-ray detection unit 23 for detecting transmission X-rays from a plurality of directions Irradiated from an X-ray beam generation source 21 and transmitted through a subject; a data acquisition unit 27 for acquiring transmission data according to the transmission X-rays detected by the X-ray detection unit; an object position detection unit 31 for detecting a position of an object inside the subject, according to a part of the transmission data acquired by the data acquisition unit; a reconstructing range determining unit 46 for determining a slice to be image-reconstructed, according to the position detected by the object position detection unit; and an image reconstruction unit 45 for reconstructing a tomographic image of a slice in which the object exists, according to the transmission data acquired by the data acquisition unit, the transmission data being acquired in the slice determined by the reconstruction range determining unit.

The object position detection unit 31 may include a transmission data extraction unit 33 for extracting transmission data at a predetermined tube position of the X-ray beam generation source, for each slice, from the transmission data acquired by the data acquisition unit, whereby to detect a position of the target object according to the extracted transmission data.

As shown in FIG. 14, the X-ray computerized tomography apparatus may further comprise a tube position determining unit 39 for determining the predetermined tube position of the X-ray beam generation source, based on the transmission data of a plurality of slices from a plurality of directions acquired by the data acquisition unit, and for sending data showing a determined tube position to the transmission data extraction unit.

Further, according to another aspect of the present invention, there is provided, as shown in FIG. 3, an X-ray computerized tomography apparatus, comprising: an X-ray detection unit 23 for detecting transmission X-rays from a plurality of directions irradiated from an X-ray beam generation source 21 and transmitted through a subject; a data acquisition unit 27 for acquiring transmission data according to the transmission X-rays detected by the X-ray detection unit; an object position detection unit 31 for detecting a position of an object inside the subject, according to a part of the transmission data acquired by the data acquisition unit: a visualizing-range detection unit 48 for determining a slice in which an image should be visualized, according to the position detected by the object position detection unit; an image reconstruction unit 45 for reconstructing a tomographic image, according to the transmission data acquired by the data acquisition unit; and a display unit 47 for visualizing the tomographic image of a slice determined by the visualizing-range detection unit.

Further, according to still another aspect of the present invention, there is provided, as shown in FIG. 24, an X-ray computerized tomography apparatus, comprising: an X-ray detection unit 23 for detecting transmission X-rays from a plurality of directions irradiated from an X-ray beam generation source 21 and transmitted through a subject; a data acquisition unit 27 for acquiring transmission data according to the transmission X-rays detected by the X-ray detection unit; an object position detection unit 31 for detecting a position of an object inside the subject, according to a part of the transmission data acquired by the data acquisition unit: and a scanning range determining unit 49 for determining a range in which the subject is to be scanned, according to the position detected by the object position detection unit.

The scanning range determining unit may alternatively be structured as a collimator controlling unit 59a shown in FIG. 19 or a collimator controlling unit 59b shown in FIG. 20, for controlling an X-ray Irradiation quantity by a shielding plate.

Further, according to still another aspect of the present invention, there is provided, as shown in FIG. 21, an X-ray computerized tomography apparatus, comprising: an X-ray detection unit 23 having detecting elements laid out in a plurality of rows in a slice direction, for detecting transmission X-rays from a plurality of directions irradiated from an X-ray beam generation source 21 and transmitted through a subject: a data acquisition unit 27 for collecting transmission data according to the transmission X-rays detected by the X-ray detection unit; an image reconstruction unit 45 for reconstructing a tomographic image of a slice in which an object inside the subject exists, according to the transmission data acquired by the data acquisition unit; and a display unit 47 for displaying an image of transmission data at a predetermined tube position of the X-ray beam generation source from among the transmission data acquired by the data acquisition unit, together with a tomographic image reconstructed by the image reconstruction nit.

Further, according to still another aspect of the present Invention, there is provided, as shown in FIG. 3, an X-ray computerized tomography apparatus, comprising: an X-ray detection unit 23 having detecting elements laid out in a plurality of rows in a slice direction, for detecting transmission X-rays for a plurality of slices from a plurality of directions irradiated from an X-ray beam generation source 21 and transmitted through a subject; a data acquisition unit 27 for acquiring transmission data according to the transmission X-rays detected by the X-ray detection unit: an object position detection unit 31 for detecting a position of an object inside the subject, according to transmission data at a predetermined tube position of the X-ray beam generation source out of the transmission data for a plurality of slices acquired by the data acquisition unit; a visualizing-range detection unit 48 for determining a slice in which an image should be visualized, according to the position detected by the object position detection unit; an image reconstruction unit 45 for reconstructing a tomographic image, according to the transmission data acquired by the data acquisition unit; and a display unit 47 for visualizing the tomographic image of a slice determined by the visualizing-range detection unit 48.

Other features and advantages of the present invention will become apparent from the following description taken in conjunction with the accompanying drawings.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 24 is a block diagram for showing a configuration of an X-ray computerized tomography apparatus according to a sixth embodiment of the present invention;

FIG. 25 is a flowchart for explaining a procedure of photographing a desired target organ inside a subject carried out by the X-ray computerized tomography apparatus according to the sixth embodiment of the present invention.

DETAILED DESCRIPTION OF THE PREFERRED EMBODIMENTS

There will be made below a detailed explanation of embodiments of an X-ray computerized tomography apparatus according to the present invention with reference to the drawings First Embodiment At first, referring to FIG. 1 to FIG. 14, an X-ray computerized tomography apparatus according to a first embodiment of the present invention will be explained in detail This first embodiment provides a function of detecting a position of an arbitrary object inside a subject according to transmission data acquired in a single slice CT apparatus having detectors in one row, and controlling a slice range in which an image is to be reconstructed and a slice range which is to be displayed, and the like on the basis of a detected position of the object.

For this purpose, according to the first embodiment, a position of an insertion object is detected by tracing the proceeding of the insertion object into a subject, for example, and a tomographic image of the slice including the tip of the insertion object is displayed. According to the first embodiment, out of projection data acquired at the time of scanning (hereinafter to be referred to as transmission data), the tip of the insertion object is detected from transmission data at an arbitrary prescribed position of a tube of an X-ray beam generation source in advance. A tomographic image of the slice in which a detected insertion object tip exists is displayed in real time (that is, sequentially after data acquisition).

Figure 1:
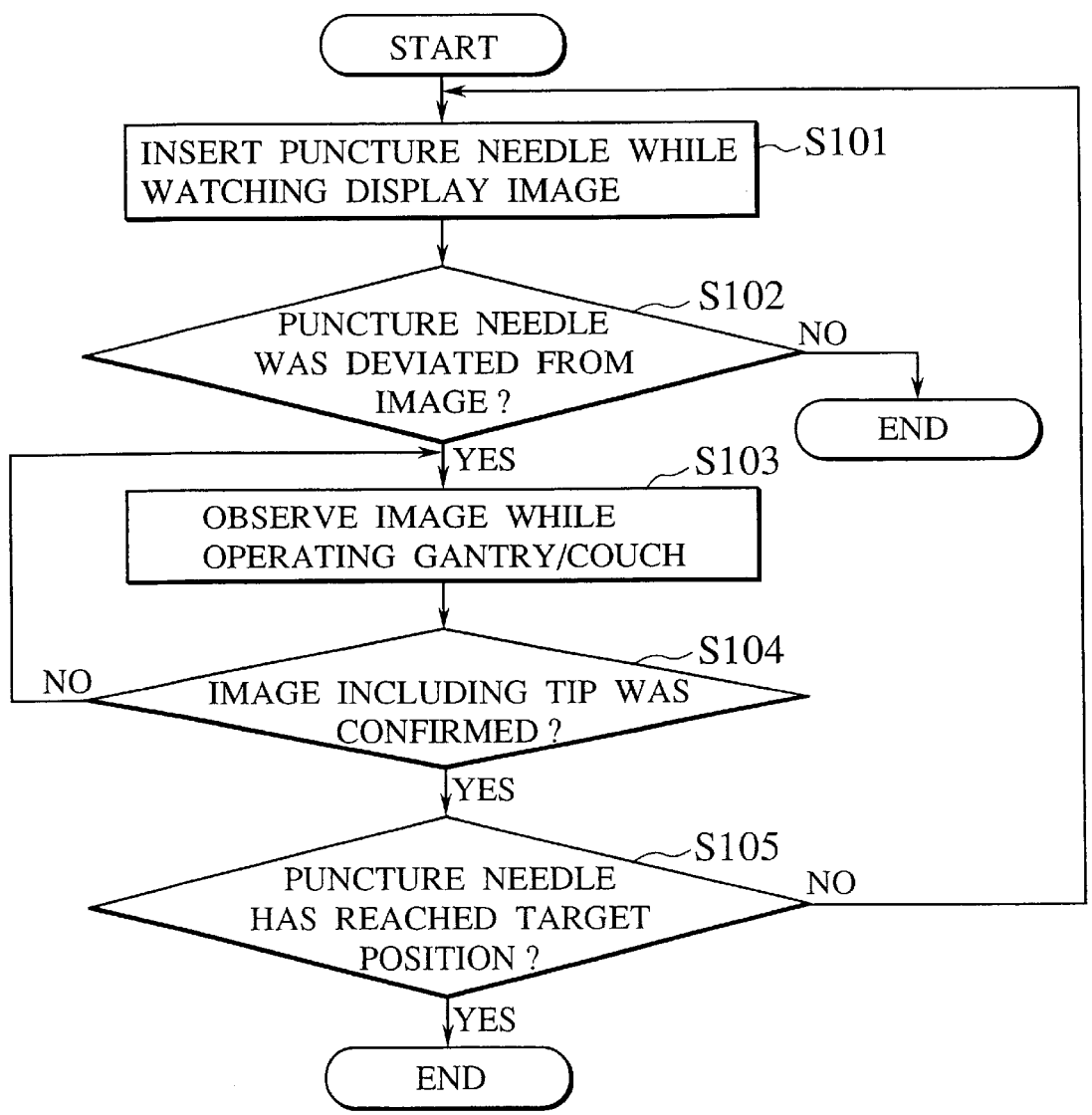
FIG. 1 is a diagram for showing a procedure of making an insertion object reach a target object within a subject according to a conventional art.
Figure 2:
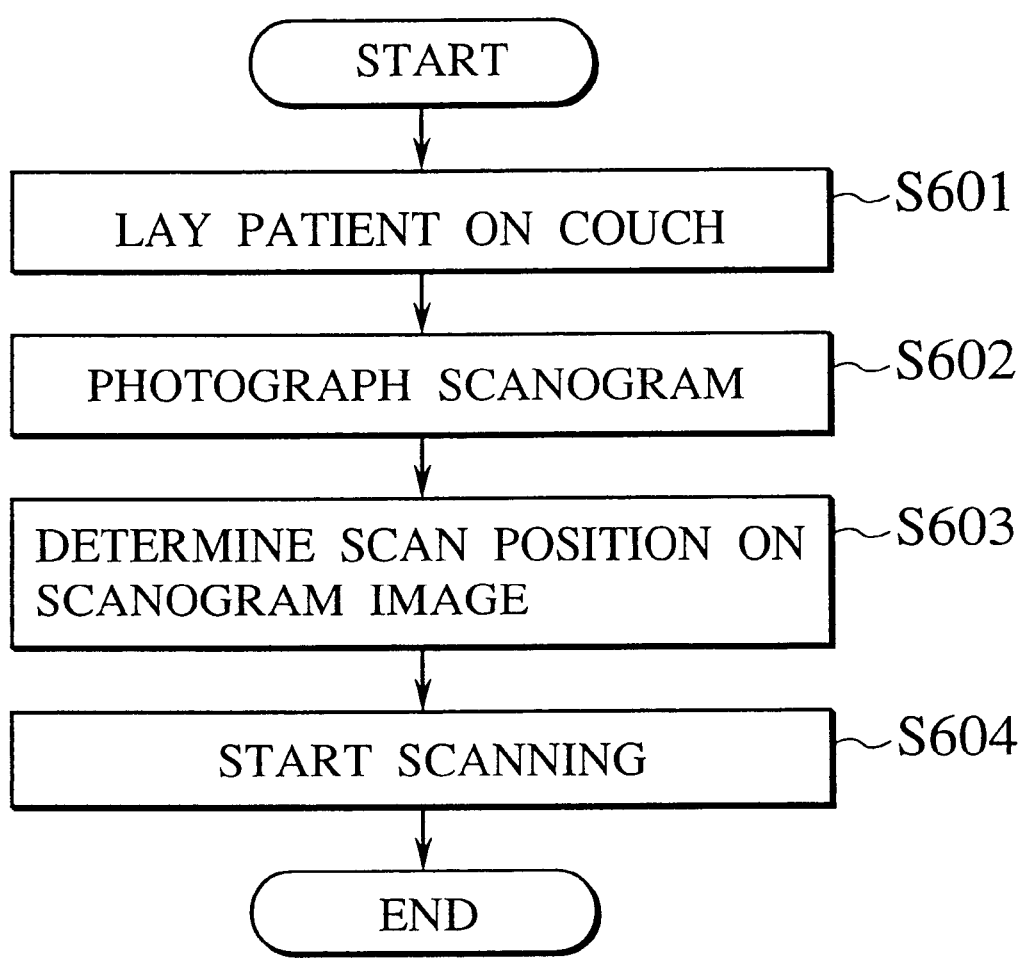
FIG. 2 is a diagram for showing a procedure of photographing a target organ inside a subject according to the conventional art.
Figure 3:
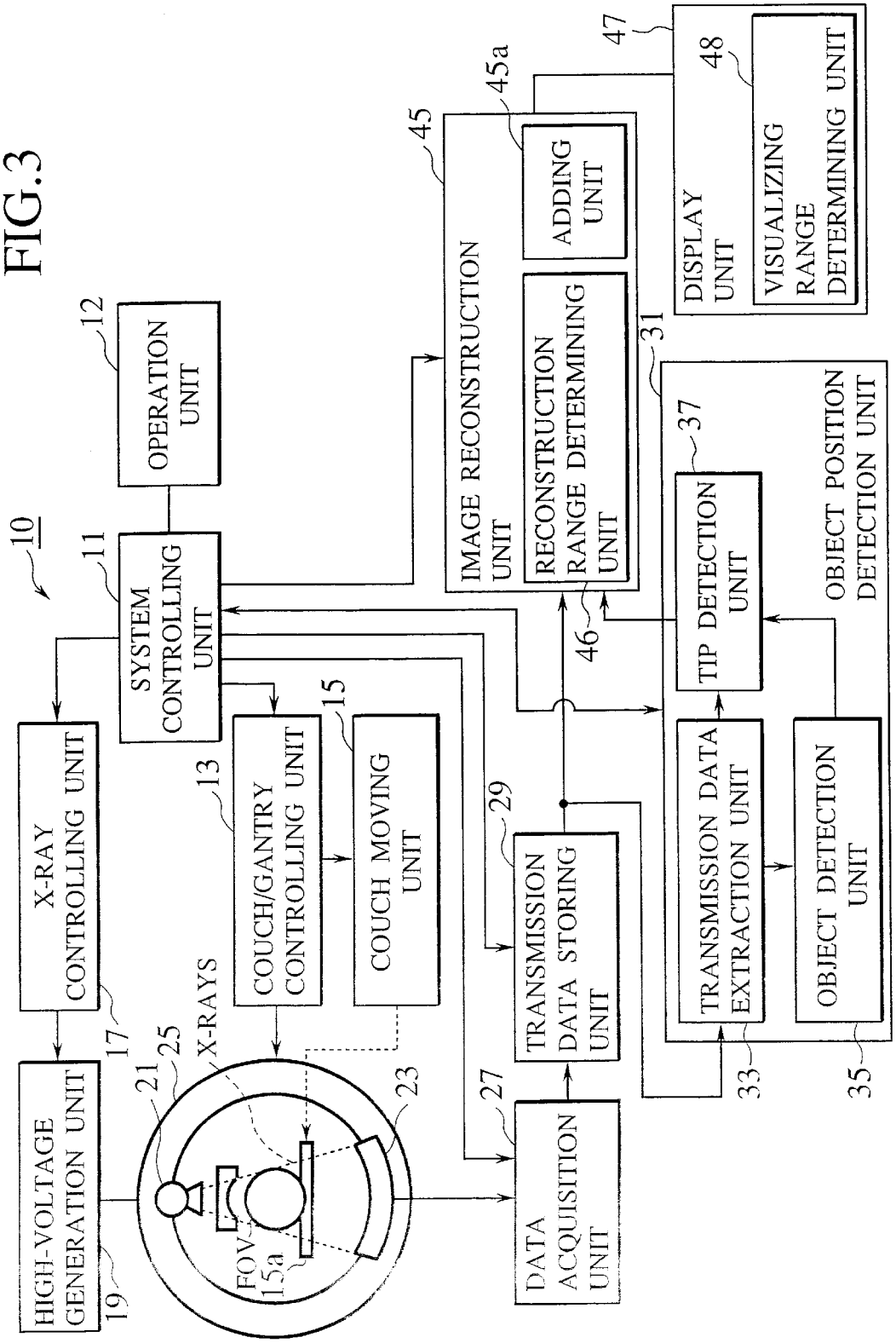
FIG. 3 is a block diagram for showing a configuration of an X-ray computerized tomography apparatus according to a first embodiment of the present invention.

FIG. 3 is a block diagram for showing a configuration of an X-ray computerized tomography apparatus according to the first embodiment of the present invention, in FIG. 3, an X-ray computerized tomography apparatus 10 according to the first embodiment comprises a system controlling unit 11, an operation unit 12, a gantry/couch controlling unit 13, a couch moving unit 15, an X-ray controlling unit 17, a high-voltage generation unit 19, an X-ray beam generation source 21, a detector 23, a rotary gantry 25, a data acquisition unit 27, a transmission data storing unit 29, an object position detection unit 31, an image reconstruction unit 45, and a display unit 47.

The X-ray computerized tomography apparatus 10 according to the first embodiment is a single-slice CT apparatus, which acquires helical data by helical scanning by using the detector 23 consisting of detectors laid out in one row, and detects an insertion object from this helical data. The helical scanning is a scanning method for helically scanning a subject by moving the subject or the gantry in a body axial direction while irradiating X-ray beams onto the subject as rotating the X-ray beam generation source 21 around the subject.

Out of helical scanning conditions including a slice thickness, a rotation speed, etc. inputted by an input unit not shown, the system controlling unit 11 outputs the rotation speed, the slice thickness, a couch move volume and the like to the gantry/couch controlling unit 13 as a gantry/couch control signal. The system controlling unit 11 outputs an X-ray beam generation control signal for controlling the generation of X-ray beams to the X-ray controlling unit 17.

The system controlling unit 11 outputs to the data acquisition unit 27 a data acquisition control signal for acquiring data. The system controlling unit 11 outputs to the object position detection unit 31 an insertion object detection control signal for detecting an insertion object such as a catheter or a puncture needle inserted into a subject.

The gantry/couch controlling unit 13 makes the rotary couch 25 rotate based on a gantry/couch control signal output from the system controlling unit 11, and outputs a couch moving signal to the couch moving unit 15. The couch moving unit 15 calculates a move volume of a couch 15a per one rotation of the rotary gantry 25, based on a couch moving signal outputted from the gantry/couch controlling unit 13, and makes the couch 15a move based on the move volume calculated. The couch 15a is structured to move in a body axial direction (that is, a direction of slices).

The X-ray controlling unit 17 controls the timing of a generation of a high voltage by the high-voltage generation unit 19, based on an X-ray beam generation control signal outputted from the system controlling unit 11. The high-voltage generation unit 19 supplies a high voltage for irradiating X-ray beams, to the X-ray beam generation source 21 based on a control signal from the X-ray controlling unit 17.

The X-ray beam generation source 21 irradiates X-ray beams in a fan shape having a thickness in a slice direction using a high voltage supplied from the high-voltage generation unit 19, onto the subject toward may directions. The detector 23 detects X-ray beams irradiated from the X-ray beam generation source 21 and transmitted through the subject.

The detector 23 consists of one row of detectors having multi-channel detecting elements. The detector 23 is structured by having detectors of, for example, about 1,000 channels arranged in an arc shape around the focus of the X-ray beam generation source 21.

The rotary gantry 25 holds the X-ray beam generation source 21 and the detector 23. Further, the rotary gantry 25 is rotated, by a gantry rotation mechanism not shown, around a rotary axis passing through an intermediate point between the X-ray beam generation source 21 and the detector 23. The rotary gantry 25 may also hold the X-ray controlling unit 17, high-voltage generation unit 19 and data acquisition unit 27.

With the above arrangement, the X-ray beam generation source 21 and the detector 23 rotate around the subject while keeping the X-ray beam generation source 21 and the detector 23 in mutually opposed disposition, and the couch 15a moves in a body axis direction at a predetermined speed. Therefore, it is possible to acquire helical data for reconstructing tomographic images of a plurality of slices.

The data acquisition unit 27 converts an output current from each detector of the detector 23 into digital data, based on a data acquisition control signal outputted from the system controlling unit 11. In this way, the data acquisition unit 27 acquires projection data (hereinafter to be referred to as transmission data) from many directions reflecting an X-ray transmission rate for each X-ray path, for a plurality of rotations (a plurality of slices), thereby to generate helical data, and outputs generated helical data. The transmission data storing unit 29 stores the helical data acquired by the data acquisition unit 27.

The object position detection unit 31 detects a position of an object such as an insertion object according to the helical data that is transmission data acquired by the data acquisition unit 27 and stored in the transmission data storing unit 29 The object position detection unit 31 further detects the tip of the insertion object (such as a puncture needle tip), and outputs position data at a position of a slice in which the tip of the insertion object exists to the image reconstruction unit 45. The details of the position detecting processing of the insertion object carried out by the object position detection unit 31 will be described later.

The image reconstruction unit 45 includes the reconstruction range determining unit 46 for controlling a range of slices in which an image should be reconstructed, based on the position data of the insertion object in the subject detected by the object position detection unit 31 and output to the image reconstruction unit 45.

First, the image reconstruction unit 45 extracts the transmission data from a plurality of view directions, from the transmission data storing unit 29. For the transmission data from the plurality of view directions, the transmission data corresponding to the slice position in which the tip of the insertion object exists is extracted the slice position indicated by the position data obtained by the object position detection unit 31. The image reconstruction unit 45 reconstructs the tomographic image of the subject at the position of the slice in which the tip of the insertion object exists, the position determined by the reconstruction range determining unit 46, based on the transmission data from the plurality of view directions.

The display unit 47 displays on a monitor device a tomographic image of the subject reconstructed by the image reconstruction unit 45. The display unit 47 includes the visualizing-range determining unit 48 for controlling a range in which the visualized image is to be generated, based on the position data of the insertion object inside the subject detected by the object position detection unit 31 and inputted via the image reconstruction unit 45 or inputted directly. The position data detected by the object position detection unit 31 may be used by both or either of the reconstruction range determining unit 46 and the visualizing-range detection unit 48 for determining respective ranges.

Figure 4:
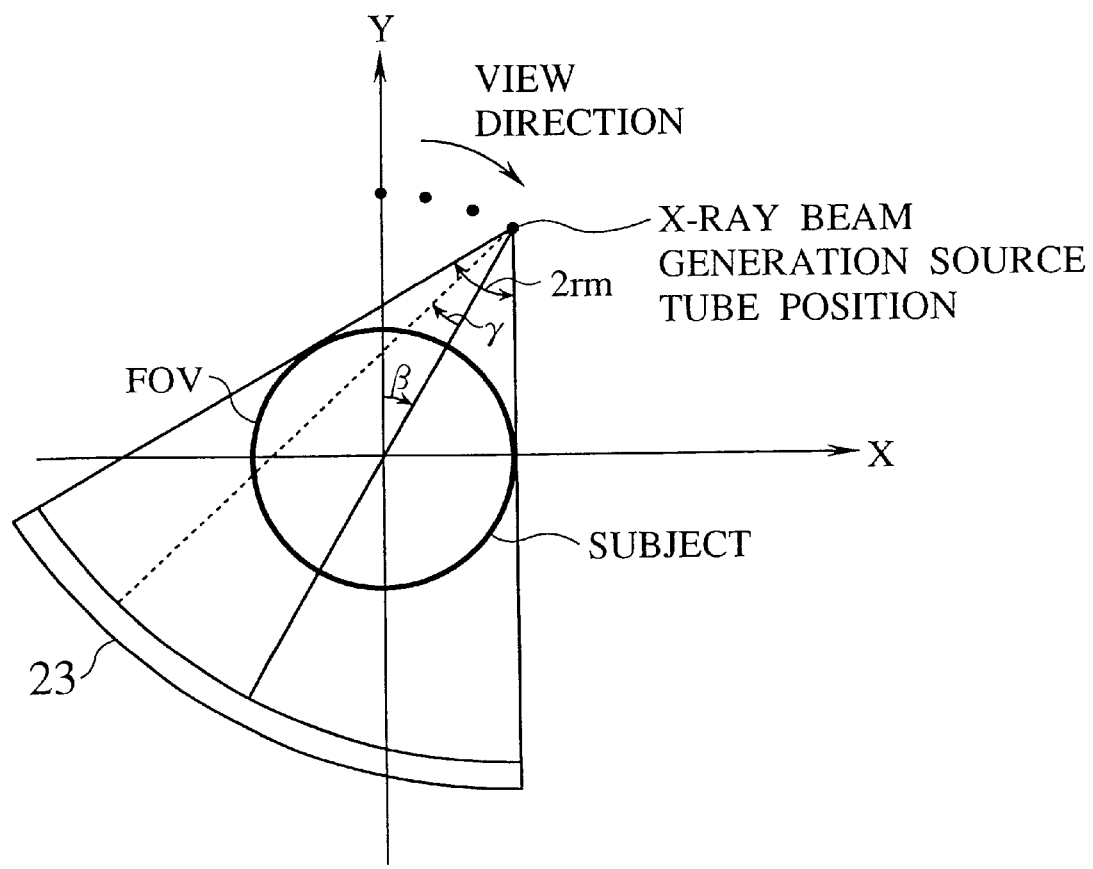
FIG. 4 is a view for explaining geometry of a third-generation X-ray computerized tomography apparatus.

Next, detailed configuration of the object position detection unit 31 will be explained. FIG. 4 shows geometry of the third-generation X-ray computerized tomography apparatus. It is assumed that a view angle formed by a linear line and the Y axis is defined as β the liner line passing through the X-ray beam generation source (a tube position) and the center of the subject, a channel angle is defined as γ, and a fan angle is defined as 2×γm. By finely changing the view angle β, data from many directions (hereinafter to be referred to as a plurality of view directions), for example, data of 1,000 views, are acquired. Note that data collection for one time will be called one view, data acquired by one detection element in one view will be called one beam, and all the beams in one view (that is, data acquired by all the detection elements) will be collectively called real data.

The object position detection unit 31 includes the transmission data extraction unit 33, an object detection unit 35 and a tip detection unit 37. The transmission data extraction unit 33 extracts, for each tube rotation, transmission data in the same view angle β, from helical data stored in the transmission data storing unit 29, The transmission data in the same view angle β is the transmission data for each tube rotation where the respective tube positions of the X-ray beam generation source 21 are at the same positions pith respect to the body axis.

The object detection unit 35 compares an X-ray absorption value of the transmission data extracted by the transmission data extraction unit 33 with a predetermined threshold value, thereby to detect a position of the insertion object according to the extracted transmission data. For example, an insertion object such as a catheter is a metal, and it has a high X-ray absorption coefficient. Therefore, it is possible to set in advance, as a threshold value, a suitable value between an X-ray absorption value of the subject and an X-ray absorption value of a metal.

The tip detection unit 37 detects a position of a'slice in which the tip of the insertion object exists, based on the position of the insertion object detected by the object detection unit 35, and outputs the position data of the slice position of the tip to the image reconstruction unit 45.

Figure 6:
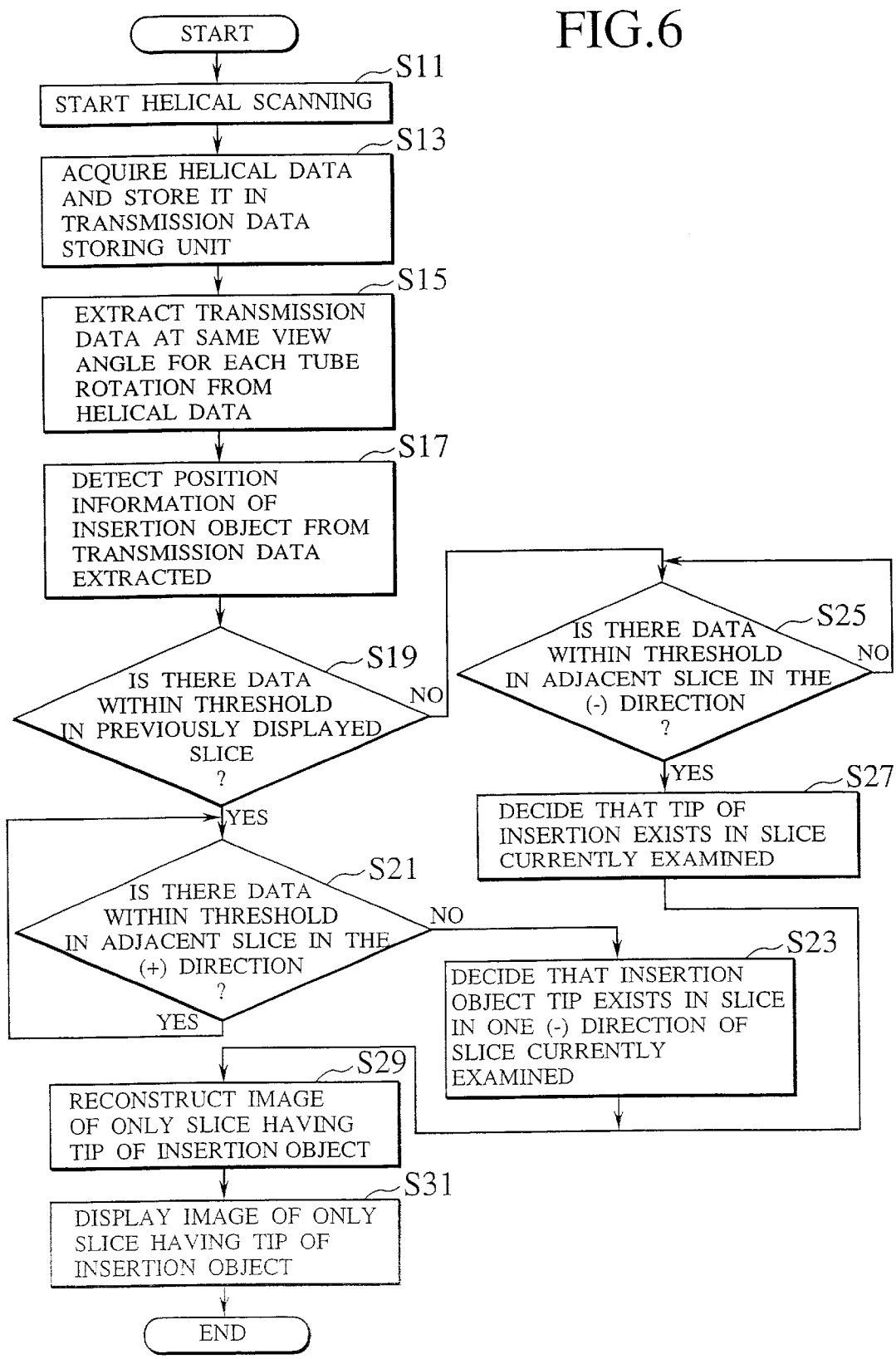
FIG. 6 is a flowchart for showing the operation of the X-ray computerized tomography apparatus according to the first embodiment of the present invention.

Next, the operation of the X-ray computerized tomography apparatus according to the first embodiment having the above-described configuration will be explained next with reference to a flowchart shown in FIG. 6.

At first, the X-ray beam generation source 21 and the detector 23 are rotated around a subject, and simultaneously the couch 15a moves in a body axial direction at a predetermined speed. In other words, a helical scanning starts (step S11).

Figure 7:
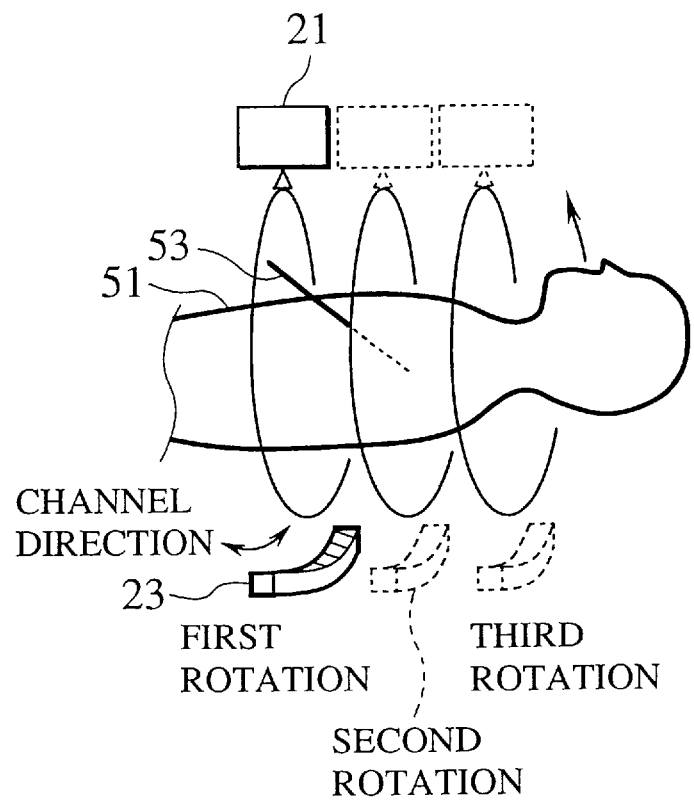
FIG. 7 is a view for explaining one example of an extraction of transmission data when a tube of an X-ray beam generation source is at an arbitrary predetermined position for each rotation, in the case that the X-ray computerized tomography apparatus according to the first embodiment carries out a helical scanning.

As shown in FIG. 7, when the X-ray beam generation source 21 and the detector 23 are continuously rotated and when the couch 15a is moved in a body axial direction at the predetermined speed, in conjunction with this rotation, the subject 51 into which the insertion object 53 is to be inserted is scanned helically along the body axial direction. With this arrangement, helical data consisting of transmission data of a plurality of slices is acquired.

The data acquisition unit 27 acquires the helical data consisting of the transmission data of the plurality of slices, by the detector 23. The acquired helical data (transmission data) is stored in the transmission data storing unit 29 (step S13).

Figure 5:
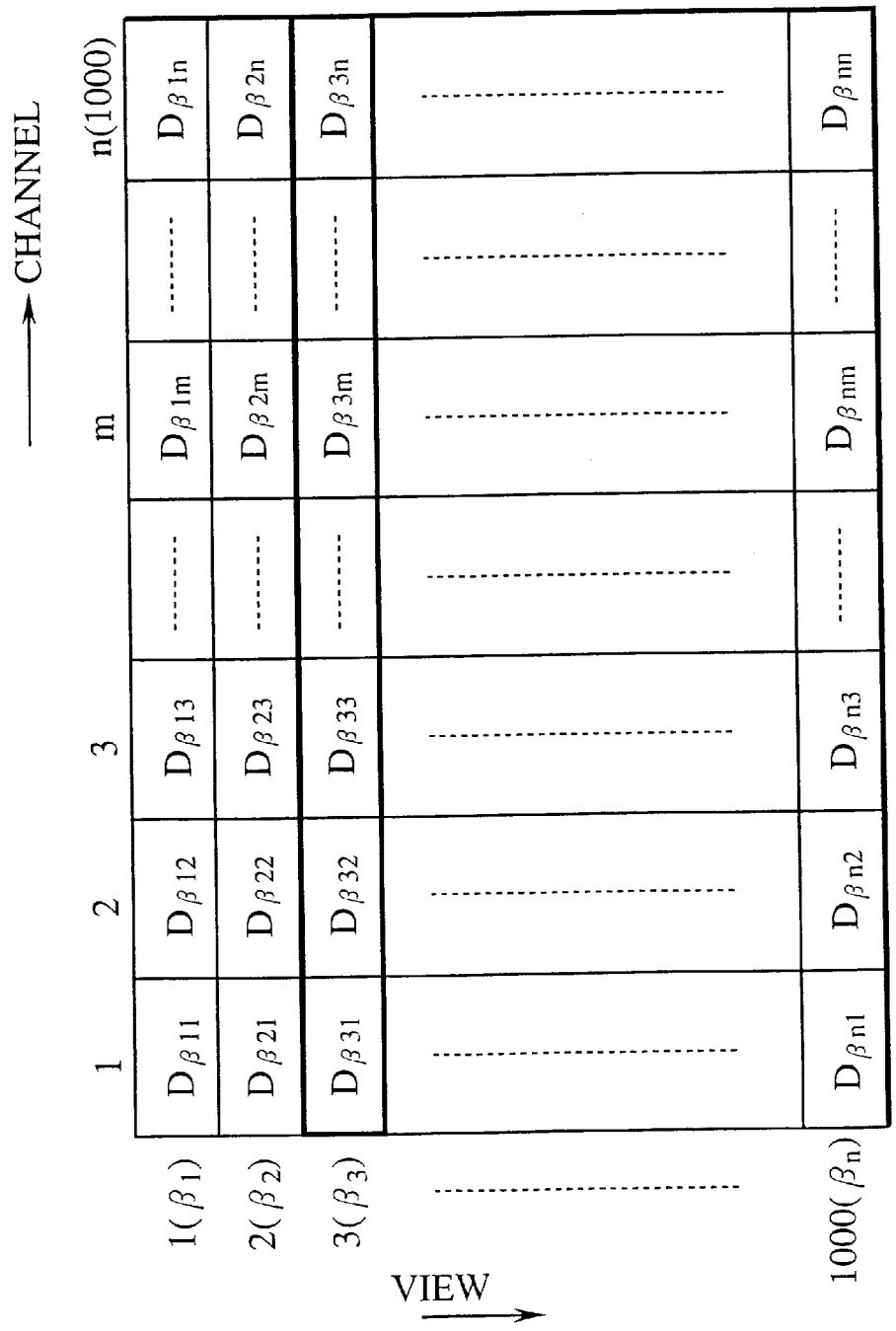
FIG. 5 is a diagram for explaining transmission data (projection data) obtained at a plurality of views.

The helical data stored in the transmission data storing unit 29 is stored as the transmission data in a plurality of 16 view directions for each slice (for each rotation). FIG. 5 shows transmission data in a plurality of view directions to be stored in the transmission data storing unit 29. The horizontal axis represents channel direction and the vertical axis represents a view direction. For example, data of 1.000 channels is stored for each view.

Next, the transmission data extraction unit 33 extracts transmission data of which view angles β are mutually identical for each tube rotation (each slice), from the helical data stored in the transmission data storing unit 29 (step S15). The transmission data at the identical view angle β is the transmission data acquired when the X-ray beam generation source 21 is at a predetermined tube position with respect to the body axis of the subject.

In other words, when the helical data is to be used for the position detection of the insertion object, only the transmission data is extracted when the tube position is at the same view angle for each rotation. For example, FIG. 7 shows an example of the extraction of transmission data when the tube is positioned just above the subject for each rotation. Not limited to this, only the transmission data at the same view angle β (for example, data of each channel at a view angle β indicated by a thick line in FIG. 5) is extracted for each rotation.

Figure 8:
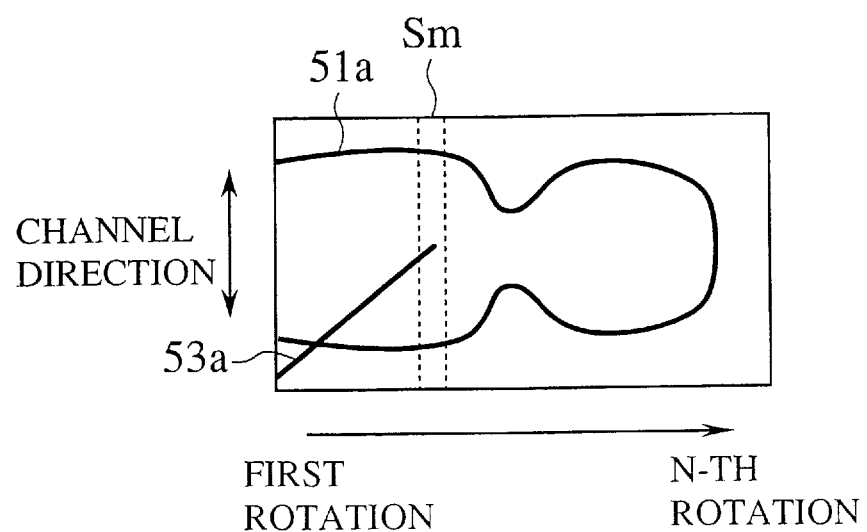
FIG. 8 is a view for showing one example of an image including an insertion object reconstructed based on transmission data obtained in a plurality of rotations shown in FIG. 7.

FIG. 8 shows an image obtained when transmission data for each rotation extracted by the transmission data extraction unit 33 is laid out along the slice direction (body axial direction). In FIG. 8, the vertical axis represents channel direction and the horizontal axis represents a number of rotations of the tube. This image includes an Image 51a of the subject and an image 53a of the insertion object 53. In other words, transmission data at certain tube position is selected, the tube position which is at a predetermined position (angle) with respect to the body axis of the subject for each rotation.

Returning back to FIG. 6, the object detection unit 35 detects a position of the insertion object 53 according to the transmission data extracted by the transmission data extraction unit 33 (step S17). The extracted transmission data includes position data of the insertion object 53. Therefore, the object detection unit 35 can detect at which position of the transmission data the insertion object 53 exists, by using data value predicted from the X-ray absorption coefficient of the insertion object 53 and the above-described threshold value.

As described above, as the insertion object 53 is a metal, this has a large X-ray absorption coefficient, and the other parts have a small X-ray absorption coefficient. Accordingly, it is easy to detect the position of the insertion object 53 using the threshold value set between these X-ray absorption coefficients. Alternatively, it is also possible to detect the position of the insertion object 53 by recognizing the shape of the insertion object 53 using a predetermined shape pattern, based on an image processing technique such as a shape-recognition image processing that is generally known.

What is important in navigating the operation using a catheter or a puncture needle is that it is possible to trace the tip of the insertion object 53 without losing sight of it until the tip reaches a target object such as a tumor. Accordingly, in promptly carrying out the operation, it is desirable that the tip of the insertion object 53 is always displayed during the operation.

For this purpose, the tip detection unit 37 further determines the tip of the insertion object 53 and detects a slice position at which the tip of the insertion object 53 exists, based on the position data of the insertion object 53 detected by the object detection unit 35, and outputs the position data of the slice position including this tip to the image reconstruction unit 45.

The image reconstruction unit 45 extracts, from the transmission data storing unit 29, the transmission data from a plurality of view directions corresponding to a slice position at which the tip of the insertion object 53 exists, obtained by the object position detection unit 31. The image reconstruction unit 45 then reconstructs the tomographic image of the subject at the slice position where the tip of the insertion object 53 exists, based or, the transmission data from the plurality of view directions. The display unit 47 displays, the image of the slice (for example, a slice Sm shown in FIG. 8) in which the tip of the insertion object 53 exists on the monitor device.

By the above-described processing, it is possible to detect in real time the insertion object 53 according to the helical data acquired, prior to the image reconstruction. Further, it is always possible to reconstruct only the image of the slice that includes the tip of the insertion object 53. Accordingly, the image of the slice that includes the tip of the insertion object 53 can be displayed in real time, after the transmission data has been acquired.

Therefore, as the state of the proceeding of the insertion object 53 into the subject can be understood by observing the tip of the insertion object 53, it is easy to carry out the operation. In other words, it is possible to carry out the navigation of the operation promptly and securely. Further, it is not necessary to use an additional part such as an insertion object supporting member for displaying the image of the slice that includes the tip, unlike the conventional art.

Figure 9:
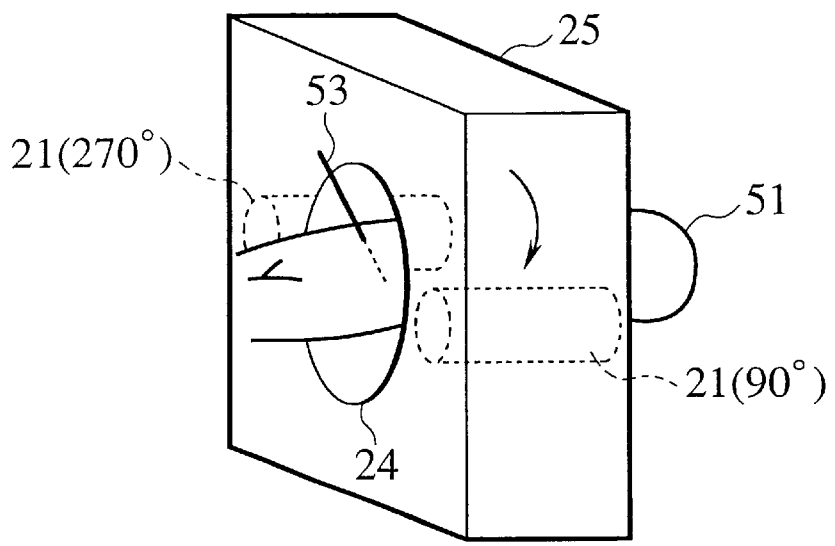
FIG. 9 is a view for explaining an extraction of transmission data when the tube is positioned at a 90-degree angle or 270-degree angle at each rotation.
Figure 10:
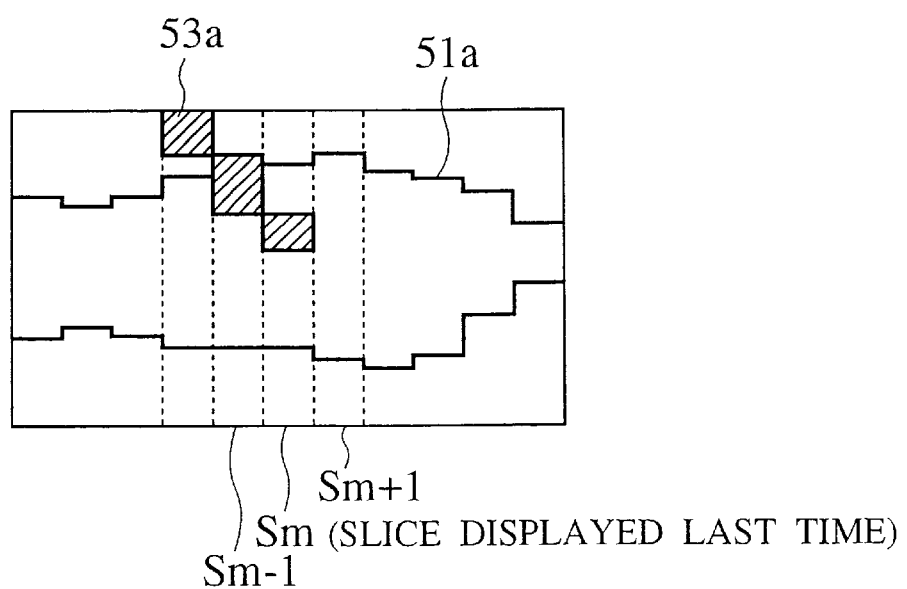
FIG. 10 is a view for showing one example of transmission data which is obtained in a plurality of rotations when the tube shown in FIG. 9 is positioned at a 90-degree or 270-degree angle.

Next, details of the processing of detecting the tip of the insertion object 53 by the tip detecting unit 37 will be explained next. In this case, it is assumed, as shown in FIG. 9, that the view angle of the tube of the X-ray beam generation source 21 of the transmission data to be extracted is 90° or 270°, for example. FIG. 10 shows data obtained by laying up the transmission data for each rotation along a slice direction, when the view angle is 90° or 270°.

Returning back to FIG. 6, at first, the tip detection unit 37 decides whether or not data within the threshold value exists in the previously displayed slice Sm (Step S19).

When the data within the threshold value exists in the previously displayed slice Sm (step S19Y), the tip detection unit 37 decides whether or not data within the threshold value (that is, the data 53a for showing the insertion object 53) exists in an adjacent slice Sm+1 in the (+) direction (step S21) When data within the threshold value exists in the adjacent slice Sm+1 in the (+) direction (step S21Y), the tip detection unit 37 further decides whether or not data within the threshold value exists in a further next adjacent slice in the (+) direction. That is, the processing in the step S21 is carried out repeatedly.

On the other hand, when data within the threshold value does not exist in the adjacent slice in the (+) direction (step S21N), the tip detection unit 37 decides that the tip of the insertion object 53 exists in the slice in one (−) direction from the slice currently being checked (step S23).

On the other hand, when data within the threshold value does not exist in the previously displayed slice Sm in the step S19 (step S19N), the tip detection unit 37 decides whether or not data within the threshold value exists in a further next adjacent slice Sm−1 in the (−) direction (step S25). When data within the threshold value does not exist in the adjacent slice Sm−1 in the (−) direction (step S25N), the tip detection unit 37 decides whether or not data within the threshold value exists in a further next adjacent slice in the (−) direction. That is, the processing in the step S25 is carried out repeatedly.

On the other hand, when data within the threshold value exists in the adjacent slice Sm−1 in the (−) direction (step S25Y), the tip detection unit 37 decides that the tip of the insertion object 53 exists in the slice currently being checked (step S27). Next, the image reconstruction unit 45 reconstructs only the image of the slice in which the tip of the insertion object 53 exists (step S29). The display unit 47 displays the image of only the slice in which the tip of the insertion object 53 exists (step S29).

As described above, the tip detection unit 37 can always detect the tip of the insertion object 53 in correspondence with the proceeding state of the insertion object 53, so that It is possible to easily carry out the operation without losing sight of the tip of the insertion object 53.

Figure 11:
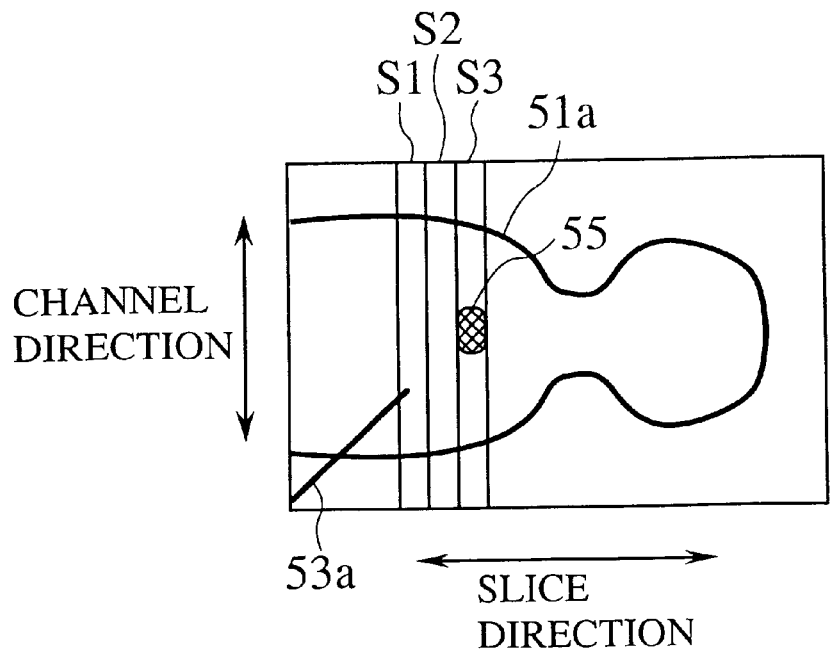
FIG. 11 is a view for showing one example of slices from a slice in which a target object of an insertion object is located to a slice in which the tip of the insertion object is located.
Figure 12:
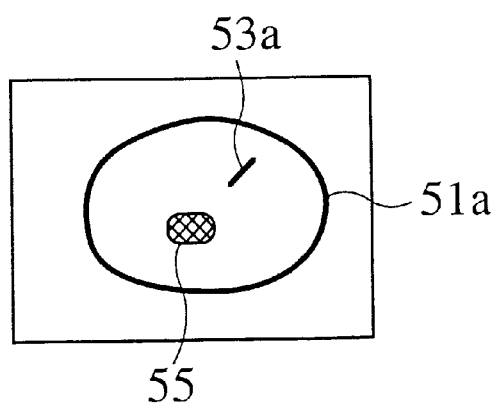
FIG. 12 is a view for showing one example of a stacked display of slices S1, S2 and 53 in FIG. 11.

In the display of the tomographic image carried out by the display unit 47, as shown in FIG. 11, it is possible to display the image by stacking slices designated on the screen in advance, such as a slice S3 in which there is the target object 55 such as a tumor, a slice S2 and a slice S1 in which there is the tip of the insertion object 53. FIG. 12 shows an example of displaying on the screen both the target object 55 and the tip of the insertion object 53 by the stacked display image. By this stacked display image, a positional relationship between the target object 55 and the tip of the insertion object 53 observed in the direction can be understood clearly. Accordingly, it is easy to make the tip of the insertion object 53 reach the target object 55, which further facilitates the operation.

In displaying the stacked display image, if the tip of the insertion object 53 is displayed in red color, or green color, for example, the positional relationship between the tip of the insertion object 53 and the target object 55 observed in the slice direction can be much easily understood. This further helps to make the tip of the of insertion object 53 easily reach the target object 55, which further facilitates the operation.

For carrying out this stacked display, an adding unit 45a is provided in the image reconstruction unit 45 of the X-ray computerized tomography apparatus 10 shown in FIG. 3. This adding unit 45a adds the transmission data of the three slices S1, S2 and S3 acquired by the data acquisition unit 27, and obtains added transmission data of the subject. The image reconstruction unit 45 may reconstruct an added tomographic image based on the added transmission data obtained, and the display unit 47 may display the added tomographic image obtained.

Figure 13:
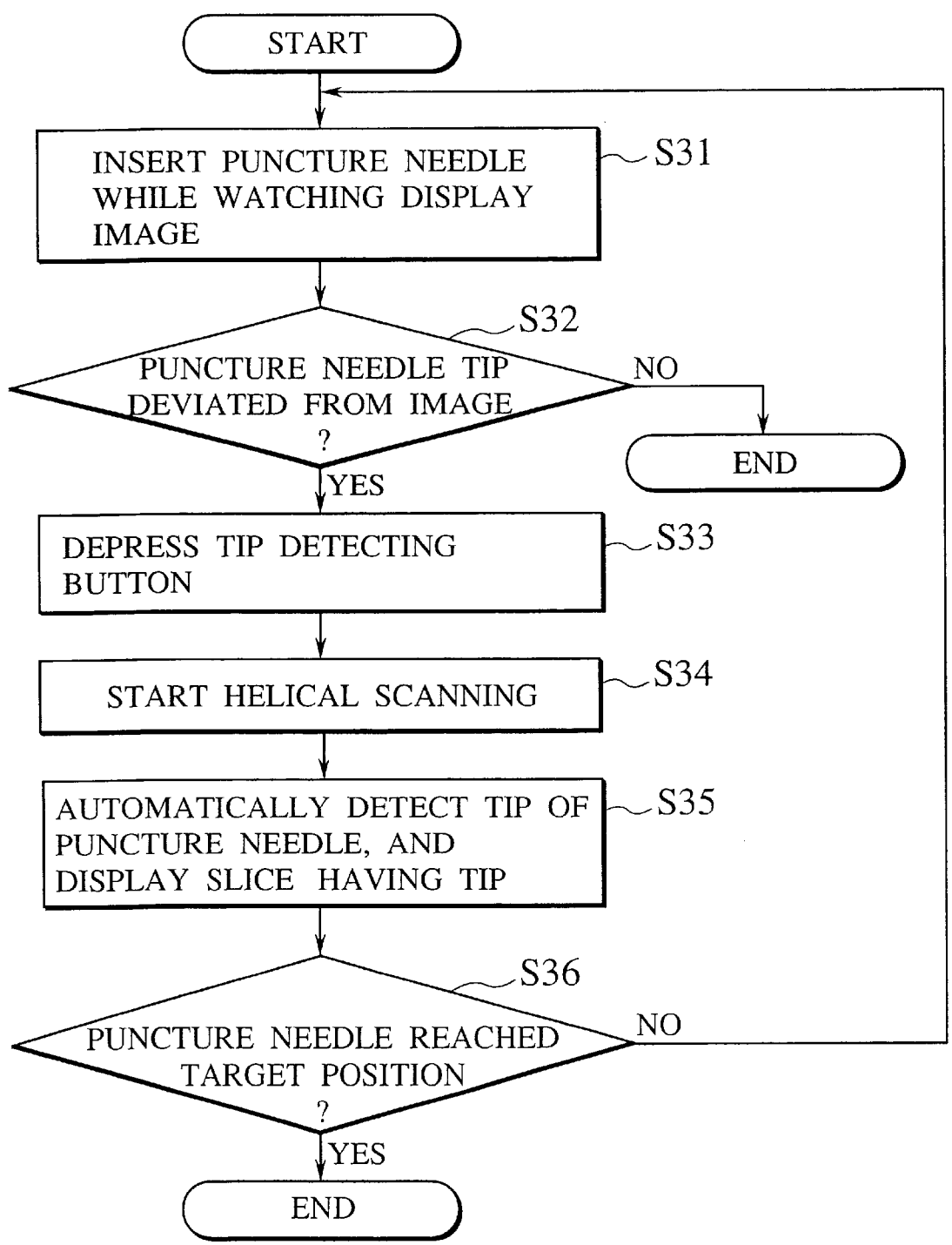
FIG. 13 is a flowchart for showing a procedure of making an insertion object reach a target object inside a subject, in the case of using the first embodiment.

Further, by storing transmission data of the slices from the Insertion object 53 to the target object 55, the distance from the tip of the insertion object 53 to the target object 55 can be suitably obtained, and this distance information may be displayed on the screen In the mean time, FIG. 13 shows a procedure of a biopsy in the case of using the first embodiment. In a single slice CT apparatus according to the first embodiment, the operator at first inserts a puncture needle into the subject while watching the image (step S11). When the puncture needle is deviated from the image displayed (step S32), the operator may simply depress a puncture needle tip detecting button to input an instruction of a puncture needle tip detection to the X-ray computerized tomography apparatus (step S33). By this input of the puncture needle tip detection instruction, the X-ray computerized tomography apparatus according to the first embodiment starts the helical scanning (step S34). Based on the transmission data obtained by this scanning, the X-ray computerized tomography apparatus detects in real time the position of the puncture needle tip, and displays the slice including the puncture needle tip (step S35). The operator may simply suitably repeat (step S36) the insertion of the puncture needle (step S31) and the depression of the puncture needle tip detection button (step S33), until the puncture needle reaches a target position. As the puncture needle tip can be detected automatically in the manner as described above, the efficiency of the operation by the operator in the CT fluoroscopy improves substantially, as compared with the conventional procedure shown in FIG. 1.

Next, as a modification of the first embodiment, there may be provided means for determining which X-ray beam tube position should be selected for determining transmission data to be used for detecting the tip of the insertion object 53.

Figure 14:
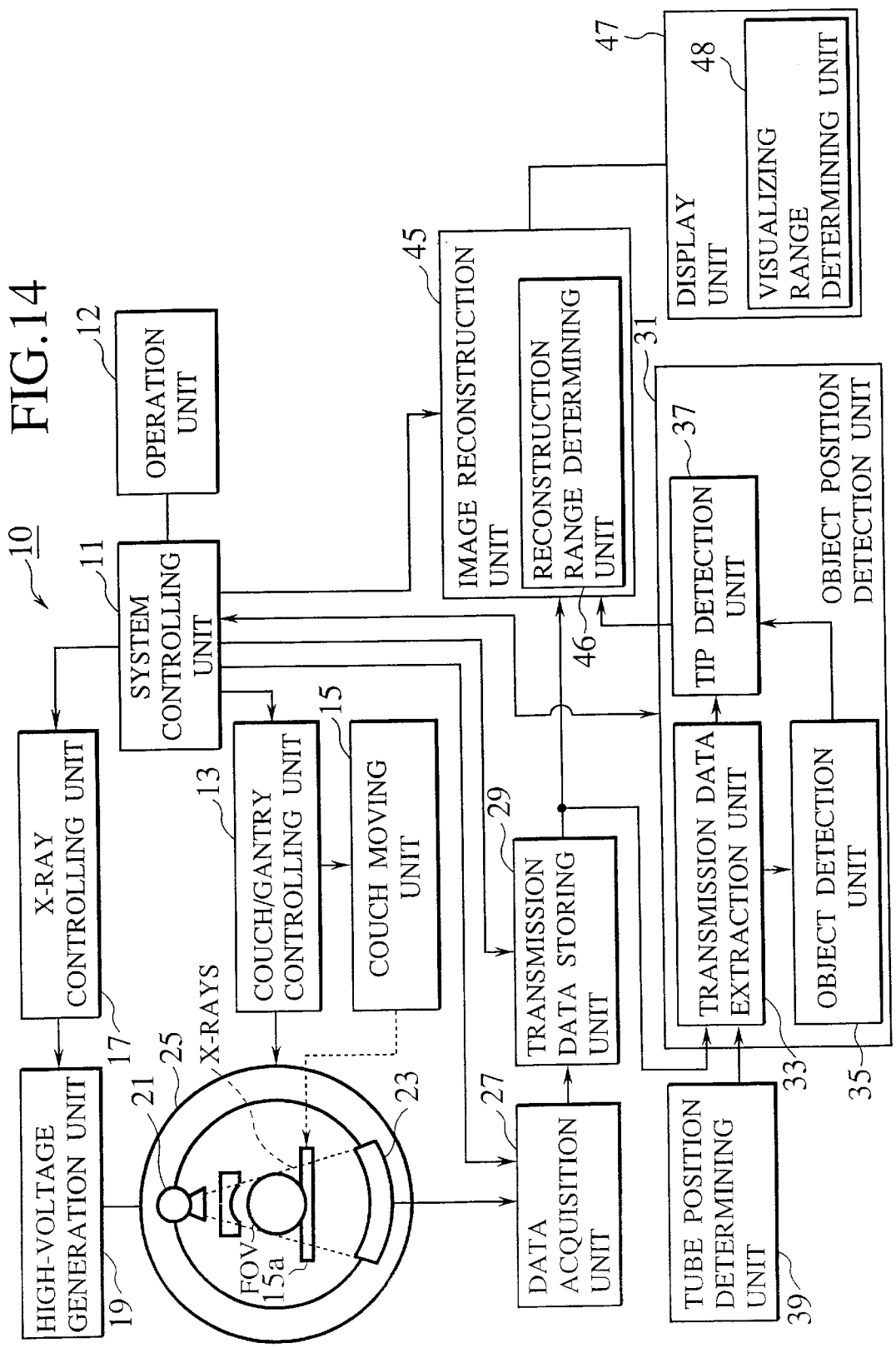
FIG. 14 is a block diagram for showing a configuration of an X-ray computerized tomography apparatus according to a modification of the first embodiment of the present invention.

FIG. 14 shows a configuration of an X-ray computerized tomography apparatus according to a modification of the first embodiment. This modification of the first embodiment is a modification of the first embodiment shown in FIG. 3 in which a tube position determining unit 39 for determining which X-ray tube position is to be extracted by the transmission data extraction unit 33 for employing transmission data is added to the configuration of the first embodiment shown in FIG. 3.

Considering a case where the insertion object 53 is inserted at an angle near a perpendicular angle with respect to a body axis at which both ends of the insertion object 53 are included in one slice, it is preferable that the tube position determining unit 39 determines an X-ray tube position as follows.

At first, out of the tube positions from 0° to 360°, several tube positions are determined in advance for every few 10°. The tube position determining unit 39 calculates the length of the insertion object 53 on the transmission data at the tube positions of these respective angles. The tube position determining unit 39 determines an angle position where the insertion object 53 has the largest length (that is, an angle position where the change of the display image due to the proceeding of the insertion object 53 becomes largest), and then outputs the determined angle position to the transmission data extraction unit 33. Thereafter, the transmission data extraction unit 33 extracts the transmission data by using the X-ray tube position at this angle position. The tube position determining unit 39 may carry out the angle position determining processing only once after starting the insertion of the insertion object 53, because it is unlikely that the angle of the insertion object 53 changes large once the insertion object 53 has been inserted into the subject.

Description has been made in the above for the case where the X-ray computerized tomography apparatus helically scans the subject. However, it should be noted that the above-described processing of the first embodiment can also be carried out in the case of what is called a scanogram for scanning a subject by moving only the couch, with the tube set at a fixed position, by using the transmission data in a plurality of couch positions in a similar manner to the transmission data of the above-described plurality of rotations.

According to the first embodiment, the following effects can be obtained. The object position detection unit 31 extracts transmission data acquired at a predetermined tube position out of the transmission data acquired by the transmission data acquisition unit 27, and detects the position of the object within a subject based on the transmission data extracted. Therefore, it is possible to detect easily and promptly the position of the object in the subject such as a tip of an insertion object, without involving an image reconstruction. Accordingly, in the CT fluoroscopy, it is possible to reconstruct in real time the tomographic image of the subject in the slice where the Insertion object exists, and to trace the tip of the insertion object. Further, as the display unit 47 can display in real time the tomographic image of the subject of the slice where the insertion object exists, the operator can understand the current position of the insertion object by watching the tip of the insertion object, and thus can carry out the operation easily. Further, as the tip detection unit 37 always detects the tip of the insertion object in correspondence with the proceeding state of the insertion object, the operator can carry out the operation easily without losing sight of the tip of the insertion object.

Second Embodiment

Figure 15:
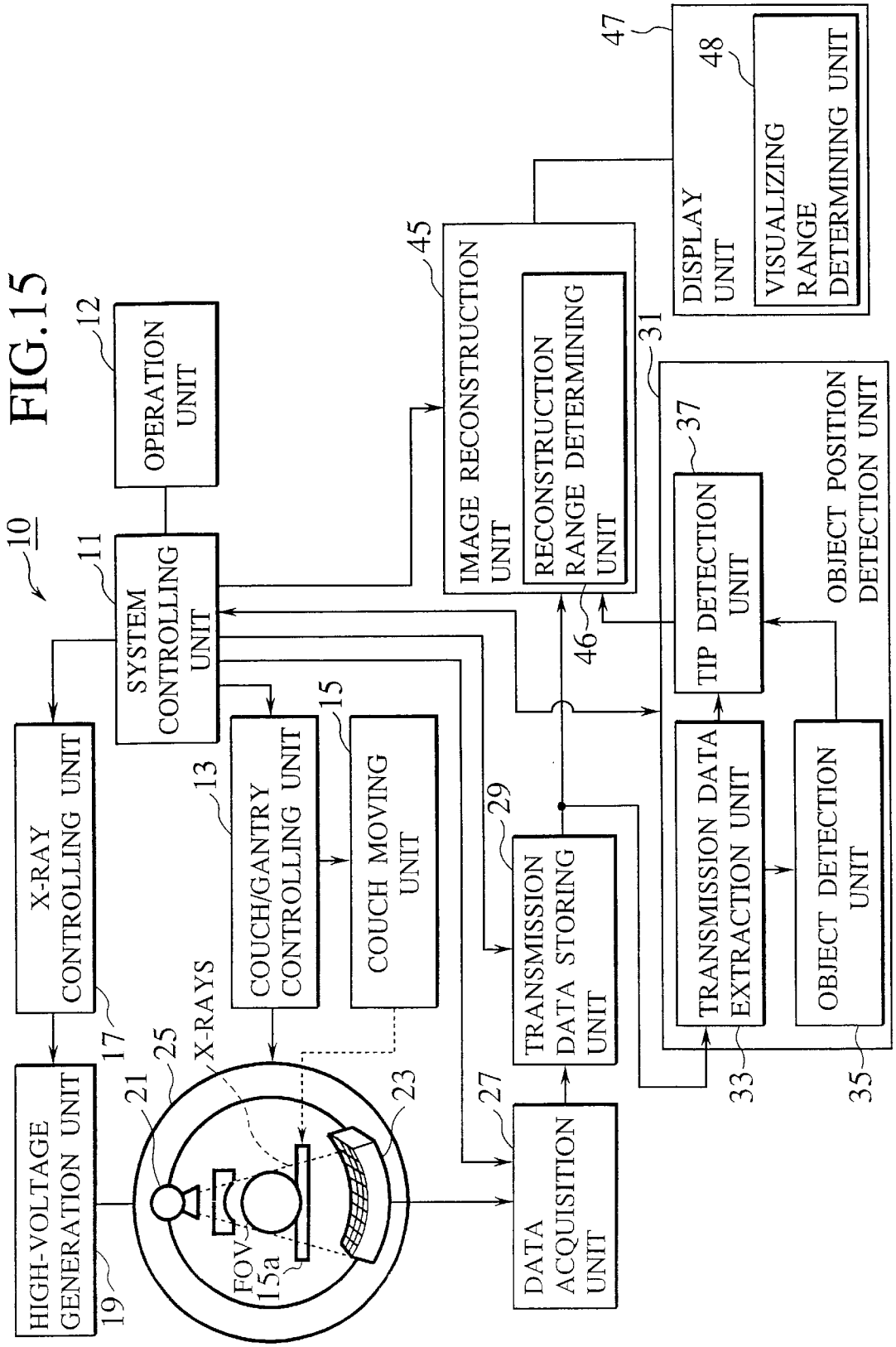
FIG. 15 is a block diagram for showing a configuration of an X-ray computerized tomography apparatus according to a second embodiment of the present invention.

Next, an X-ray computerized tomography apparatus according to a second embodiment of the present invention will be explained in detail with reference to FIG. 15 to FIG. 18. This X-ray computerized tomography apparatus according to the second embodiment provides a similar function to that of the first embodiment of detecting a position of the insertion object 53, based on volume data that is transmission data obtained by rotating the rotary gantry by one rotation, by using a two-dimensional detector (a plane detector) consisting of detector elements formed in a plurality of detector rows. According to what is called the multi-slice X-ray computerized tomography apparatus using this two-dimensional detector, it is possible to scan a subject at a higher speed than using the detector having detector elements in one row, and therefore, this multi-slice X-ray computerized tomography apparatus is suitable for a more real-time processing FIG. 15 shows a configuration of the X-ray computerized tomography apparatus according lo the second embodiment of the present invention. This second embodiment is a modification of the first embodiment shown in FIG. 3, in which the detector 23 structured in one row for a single slice shown in FIG. 1 has been replaced by a plane detector 23a structured by a plurality of rows for multi-slices. Other configurations of the second embodiment are the same as those of the first embodiment shown in FIG. 3.

Figure 16:
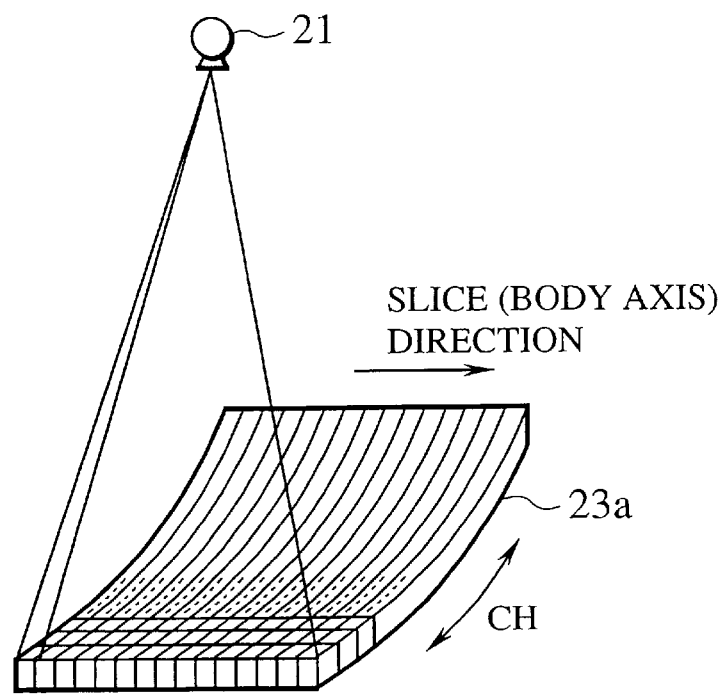
FIG. 16 is a view for showing a two-dimensional detector having detecting elements arranged in a plurality of rows in a direction of slices according to the second embodiment.

FIG. 16 shows a configuration of the X-ray beam generation source 21 and the plane detector 23a of the X-ray computerized tomography apparatus according to the second embodiment of the present invention. The plane detector 23a consists of multi-channel detecting elements, and forms a two-dimensional detector having these detecting elements laid out in a plurality of rows in a slice direction. In each row of the detecting elements of the plane detector 23a, detecting elements of about 1,000 channels are arranged in an arc shape around the focus of the X-ray beam generation source 21, in a similar manner to the single slice X-ray computerized tomography apparatus.

Figure 17:
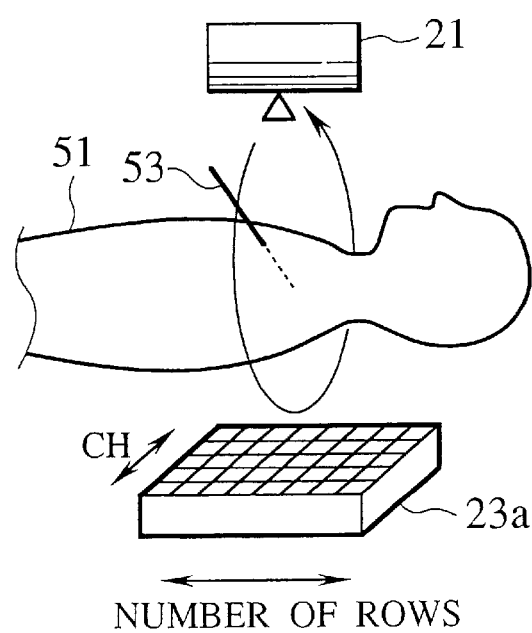
FIG. 17 is a view for explaining a scanning by the two-dimensional detector shown in FIG. 16.

FIG. 17 shows a data acquisition in the second embodiment. When the X-ray beam generation source 21 and the plane detector 23a having the configuration as shown in FIG. 16 make one rotation around the subject 51, volume data that is transmission data from many directions for a plurality of slices are acquired.

The transmission data extraction unit 33 of the second embodiment extracts volume data at predetermined one tube position out of the volume data acquired.

Figure 18:
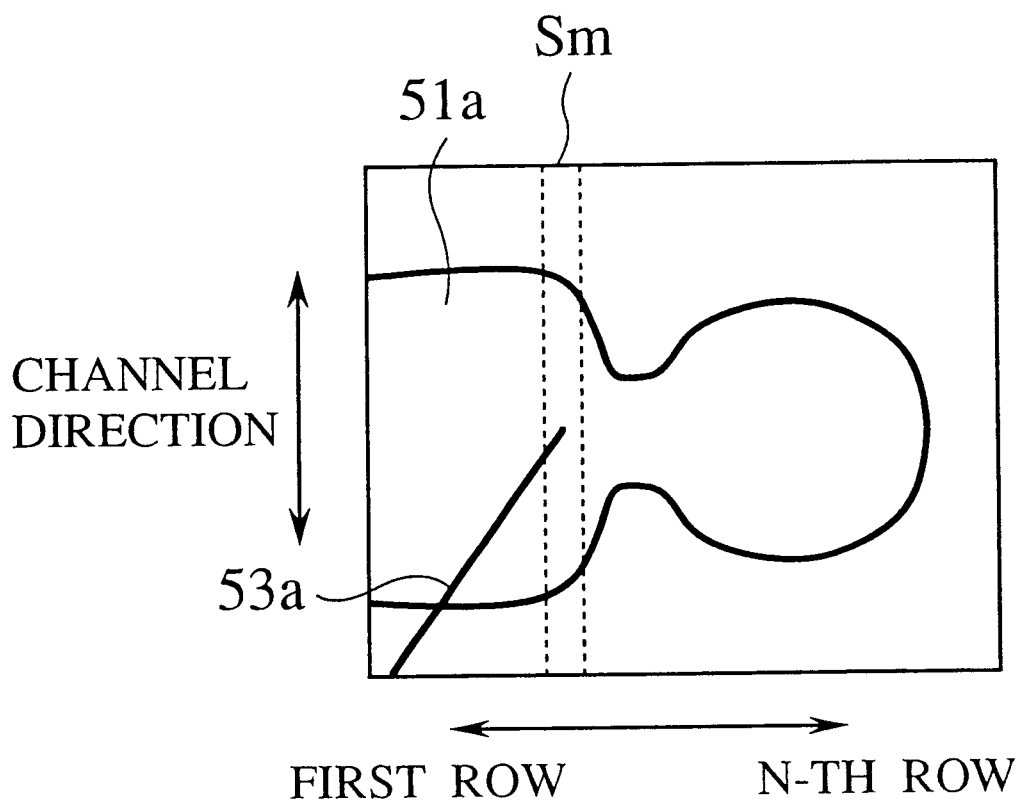
FIG. 18 is a view for showing an image including an insertion object obtained by extracting transmission data when a tube is located at an arbitrary predetermined position, out of volume data obtained by volume scanning, according to the second embodiment.

FIG. 18 shows an image obtained by laying out the extracted volume data in a direction of the plane detector (that is, in a slice direction). The image shown in FIG. 18 is similar to the image shown in FIG. 8, and includes an image 51a of the subject 51 and an image 53a of the insertion object 53. In this manner, the object position detection unit 31 can detect a position where the tip of the insertion object exists according to the volume data (transmission data). The image reconstruction unit 45 can reconstruct the image of only the transmission data of the slice Sm shown in FIG. 12 or display the image, by carrying out a similar processing to that of the first embodiment.

In the multi-slice CT apparatus according to the second embodiment, the operator's procedure taken for the CT fluoroscopy shown in FIG. 13 becomes simpler. When the operator inserts the puncture needle while watching the Image, the X-ray computerized tomography apparatus according to the second embodiment can automatically detect a position of the puncture needle tip and can always display the image of the slice including the detected puncture needle tip. Therefore, the efficiency of the operation by the operator in the CT radiography improves substantially.

According to the second embodiment, the following effects can be obtained. In the X-ray computerized tomography apparatus (multi-slice CT) according to the second embodiment, it is also possible to detect a position of the insertion object 53 in similar manner to the helical scanning by the X-ray computerized tomography apparatus having detecting elements in one row (single-slice CT) according to the first embodiment. Therefore, It is possible to obtain a similar effect to that of the first embodiment- As the multi-slice CT can scan the subject at a higher speed, it is possible to reconstruct and display an image of a part including a desired object in more real time.

In the case that a helical scanning is carried out by using the plane detector 23a in the second embodiment, only the transmission data where the tube position is mutually identical is used in a similar manner to the method of using helical data as explained in the first embodiment.

Third Embodiment

Next, an X-ray computerized tomography apparatus according to a third embodiment of the present invention will be explained in detail with reference to FIG. 19.

In the above-described embodiments, a range in which an image is to be reconstructed or a range in which an image is to be visualized is determined based on a position of art object detected by the object position detection unit 31. On the other hand, in the third embodiment, only a necessary range is irradiated, based on position data of the object.

In other words, the third embodiment provides a function of controlling the collimator so as to irradiate on only a photographing area from the tip of the insertion object 53 to the target object, in the X-ray computerized tomography apparatus of the second embodiment equipped with a plurality of rows of detectors. By controlling this collimator, it is possible to decrease unnecessary exposure of the subject to X-rays.

Figure 19:
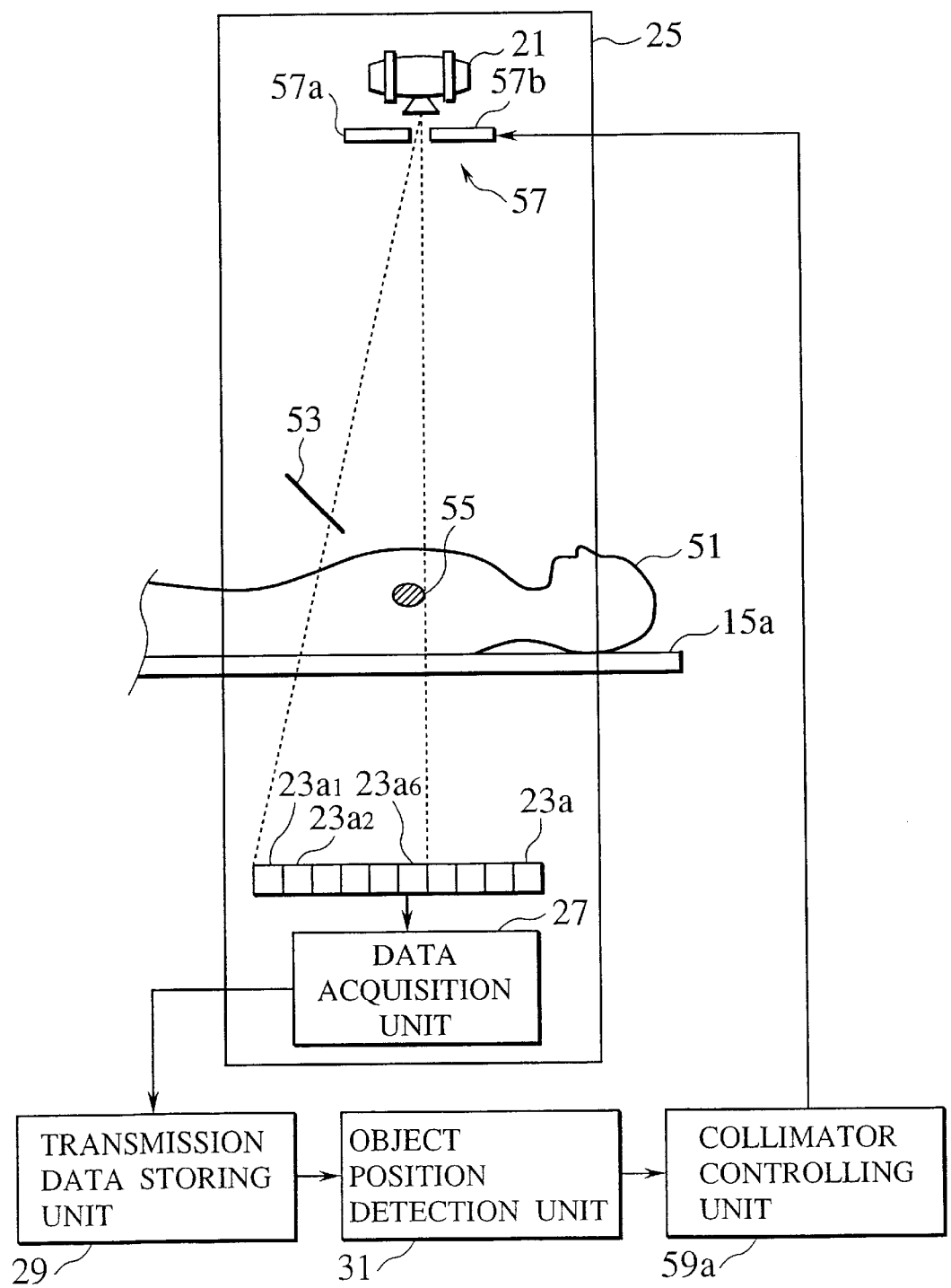
FIG. 19 is a block diagram for showing a configuration of an X-ray computerized tomography apparatus according to a third embodiment of the present invention.

FIG. 19 is a block diagram for showing key elements of the configuration of the X-ray computerized tomography apparatus according to the third embodiment of the present invention. The third embodiment is a modification of the second embodiment shown in FIG. 15 in which a collimator 57 arranged between the subject 51 and the X-ray beam generation source 21, and a collimator controlling unit 59a for controlling the operation of the collimator 57 based on position data of an object detected by the object position detection unit 31 are added to the configuration of the second embodiment.

As shown in FIG. 19, the X-ray beam generation source 21 and the plane detector 23a are disposed face to face to sandwich the subject 51, and the collimator 57 is disposed between the subject 51 and the X-ray beam generation source 21. The collimator 57 has two X-ray shielding plates 57a and 57b movable along the slice direction.

The transmission data storing unit 29 stores volume data acquired by the data acquisition unit 27. In the object position detection unit 31, the transmission data extraction unit 33 extracts volume data at one tube position from the transmission data (volume data) stored in the transmission data storing unit 29. The object detection unit 35 and the tip detection unit 37 detect a position of a slice in which the tip of the insertion object 53 exists and a position of a slice in which a target object exists according to the volume data extracted.

The collimator controlling unit 59a controls the width between the two X-ray shielding plates 57a and 57b of the collimator 57, based on the position of the slice in which the tip of the insertion object 53 exists and the position of the slice in which the target object exists, the positions being detected by the object position detection unit 31. More specifically, the collimator controlling unit 59a controls the collimator 57 in a width to irradiate X-rays onto only the photographing area from the tip of the insertion object 53 to the target object 55. In other words, the collimator controlling unit 59a controls the X-ray beam thickness and irradiates X-rays onto only the photographing area of the subject corresponding to a part of detectors 23a1 to 23a6 within the plane detector 23a laid out in a plurality of rows. Accordingly, it is possible to decrease unnecessary exposure of the subject to X-rays.

The image reconstruction unit 45 according to the third embodiment may reconstruct and display an image of transmission data of the whole slices obtained by one-time scanning stored in the transmission data storing unit 29. Alternatively, the image reconstruction unit 45 may reconstruct and display an image of only transmission data of a part of slices, based on position data obtained by the object position detection unit 31, in a similar manner to the first and second embodiments.

According to the third embodiment. X-rays are irradiated onto the subject in only the area between the insertion object and the target object 55 of the insertion object detected by the object position detection unit 31, as a photographing area. Therefore, it is possible to decrease unnecessary exposure of the subject to X-rays.

Fourth Embodiment

Next, an X-ray computerized tomography apparatus according to a fourth embodiment of the present invention will be explained in detail with reference to FIG. 20. This fourth embodiment provides a function of controlling the collimator so as to irradiate X-rays onto only the photographing area corresponding to two slices of a slice in which the tip of the insertion object 53 exists and an adjacent slice in a direction of inserting this insertion object 53. In the X-ray computerized tomography apparatus of the second embodiment equipped with a plurality of row of detectors. By controlling this collimator, it is possible to further decrease unnecessary exposure of the subject to X-rays. The X-rays irradiation onto these two slices only is effective when it is not necessary to display the target object 55 on the screen. According to the fourth embodiment, the display unit 47 always displays only the two slices of the slice in which the tip of the insertion object 53 exists and the adjacent slice in the proceeding direction of the insertion object 53, tracing the proceeding of the insertion object 53.

Figure 20:
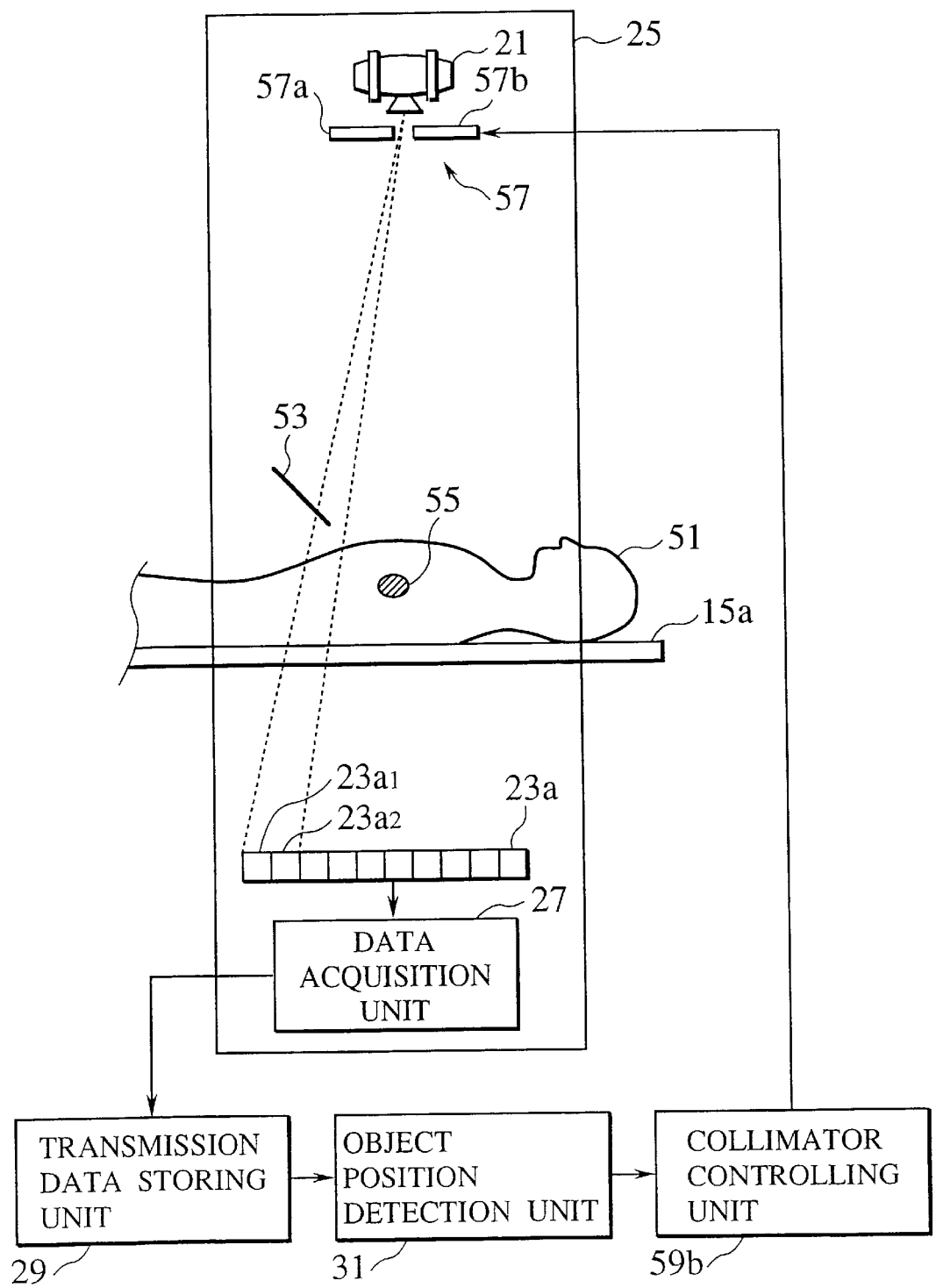
FIG. 20 is a block diagram for showing a configuration of an X-ray computerized tomography apparatus according to a fourth embodiment of the present invention.

FIG. 20 is a block diagram for showing key parts of the configuration of the X-ray computerized tomography apparatus according to the fourth embodiment of the present invention. The fourth embodiment is a modification of the third embodiment shown in FIG. 19 in which the collimator controlling unit 59a in the third embodiment shown in FIG. 19 has been replaced with the collimator controlling unit 59b shown in FIG. 20.

As shown in FIG. 20, the X-ray beam generation source 21 and the plane detector 23a are disposed face to face to sandwich the subject 51, and the collimator 57 is disposed between the subject 51 and the X-ray beam generation source 21. The collimator 57 has two X-ray shielding plates 57a and 57b movable along the slice direction.

The transmission data storing unit 29 stores volume data acquired by the data acquisition unit 27. In the object position detection unit 31, the transmission data extraction unit 33 extracts volume data at one tube position from the transmission data (volume data) stored in the transmission data storing unit 29. The object detection unit 35 and the tip detection unit 37 detect a position of a slice in which the tip of the insertion object 53 exists and a position of an adjacent slice in a proceeding direction of the insertion object.

The collimator controlling unit 59b controls the width between the two X-ray shielding plates 57a and 57b of the collimator 57, based on the position of the slice in which the tip of the insertion object 53 exists and the position of the slice adjacent to the proceeding direction of the insertion object 53, the positions being detected by the object position detection unit 31. More specifically, the collimator controlling unit 59b controls the collimator 57 in a width to irradiate X-rays onto only the photographing area of the slice in which the tip of the insertion object 53 exists and the slice adjacent to the proceeding direction of the insertion object 53. In other words, the collimator controlling unit 59b controls the X-ray beam thickness and irradiates X-rays onto only the photographing area of the subject corresponding to a part of detectors 23a1 and 23a2 within the plane detector 23a laid out in a plurality of rows. Accordingly, it is possible to further decrease unnecessary exposure of the subject to X-rays.

The image reconstruction unit 45 according to the fourth embodiment may reconstruct and display an image of transmission data of the whole slices obtained by one-time scanning stored in the transmission data storing unit 29. Alternatively, the image reconstruction unit 45 may reconstruct and display an image of only transmission data of a part of slices, based on position data obtained by the object position detection unit 31, in a similar manner to the first and second embodiments According to the fourth embodiment, X-rays are irradiated onto the subject in only the area of the slice in which the insertion object exists and the slice adjacent to the proceeding direction of the insertion object detected by the object position detection unit 31, as a photographing area. Therefore, it is possible to further decrease unnecessary exposure of the subject to X-rays. Note that whether the target object of the insertion object inside the subject should be displayed or not may be designated by the operator or the doctor (to be simply described as the operator) from an input unit not shown.

Fifth Embodiment

Next, an X-ray computerized tomography apparatus according to a fifth embodiment of the present invention will be explained in detail with reference to FIG. 21 to FIG. 23. This X-ray computerized tomography apparatus according to the fifth embodiment provides a function of displaying volume data that is transmission data obtained by rotating the rotary gantry by one rotation, together with the image-reconstructed tomographic image, by using a two-dimensional detector (a plane detector) consisting of detector elements formed in a plurality of detector rows. For example, in a CT fluoroscopy, it is possible to simultaneously display a tomographic image including the tip of the insertion object and The transmission data at a predetermined position of a tube. With the above arrangement, the operator can observe a proceeding state of the insertion object inside the subject, from a plurality of directions such as three directions, for example.

Figure 21:
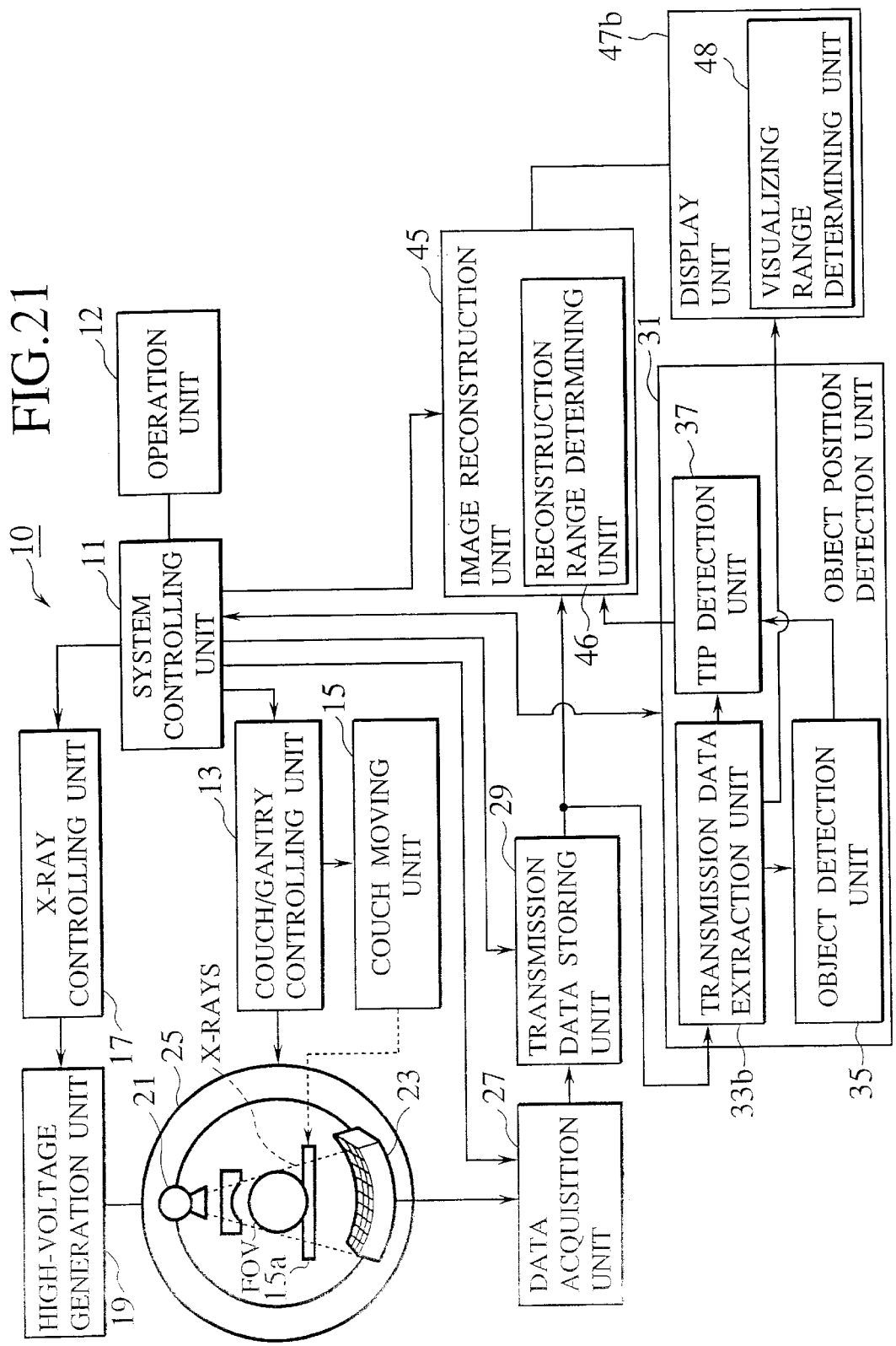
FIG. 21 is a block diagram for showing a configuration of an X-ray computerized tomography apparatus according to a fifth embodiment of the present invention.

FIG. 21 shows a configuration of the fifth embodiment of the present invention. The fifth embodiment is a modification of the second embodiment shown in FIG. 15 in which the transmission data extraction unit 33 shown in FIG. 15 has been replaced by a transmission data extraction unit 33b shown in FIG. 21, and the display unit 47 shown in FIG. 15 has been replaced by a display unit 47b shown in FIG. 21. Other configurations of the fifth embodiment are similar to those of the second embodiment shown in FIG. 15.

Figure 22:
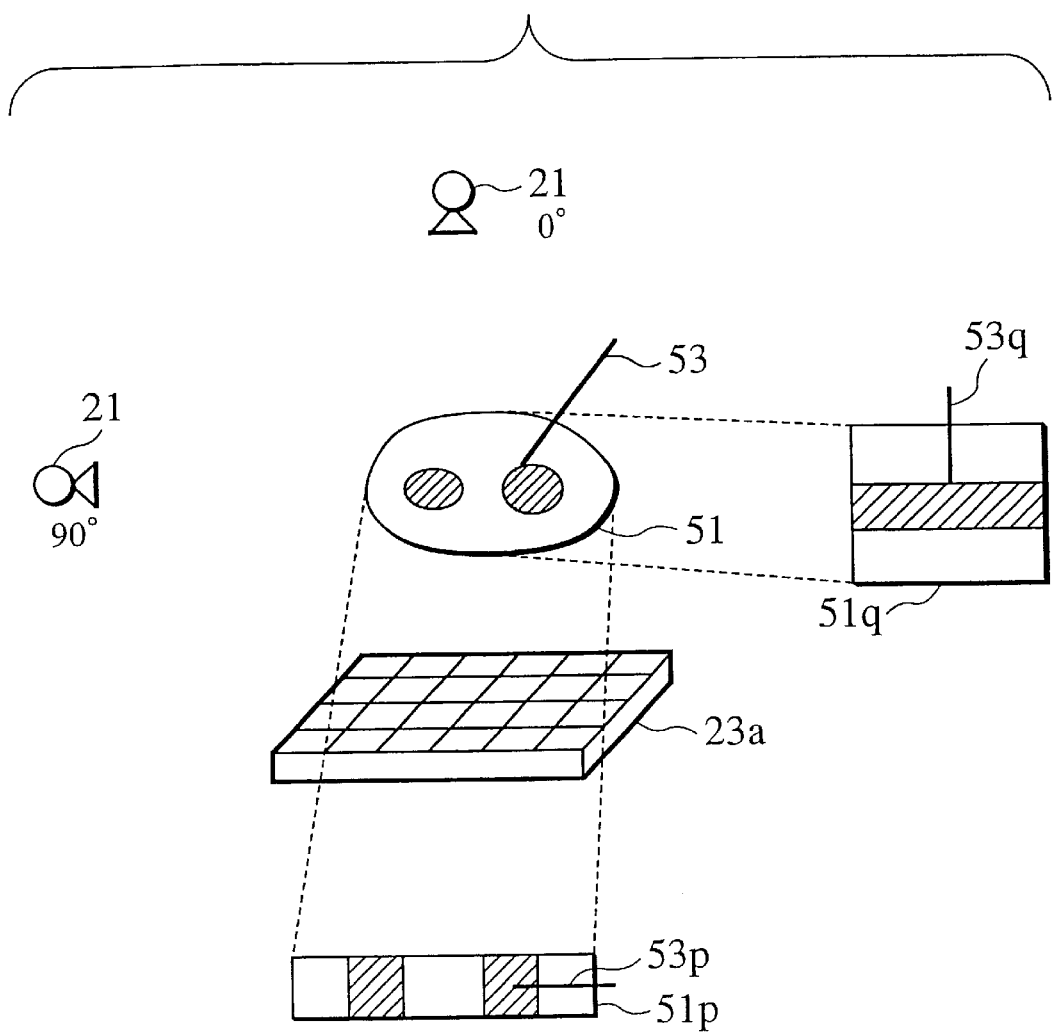
FIG. 22 is a view for explaining the obtaining of transmission data at a plurality of tube positions according to the fifth embodiment.

FIG. 22 shows a transmission data extraction to be carried out by the transmission data extraction unit 33b in the object position detection unit 31 of the fifth embodiment. The transmission data extraction unit 33b extracts the transmission data in a plurality of slices at one tube position as explained in the second embodiment. Further, based on the position data of the insertion object 53 detected by the object detection unit 35, the transmission data extraction unit 33b extracts the transmission data at arbitrary plural positions of the slice including the tip of the insertion object 53 detected by the object detection unit 35, as display data. Fox example, in FIG. 22. transmission data where the tube position is at an angle of 0° and 90° (51p, 53p, 51q, 53g) are extracted respectively.

The image reconstruction unit 45 reconstructs the Image of the tomographic image of the slice in which the insertion object 53 exists, based on position data of the slice in which the insertion object 53 exists, obtained by the object position detection unit 31.

Figure 23:
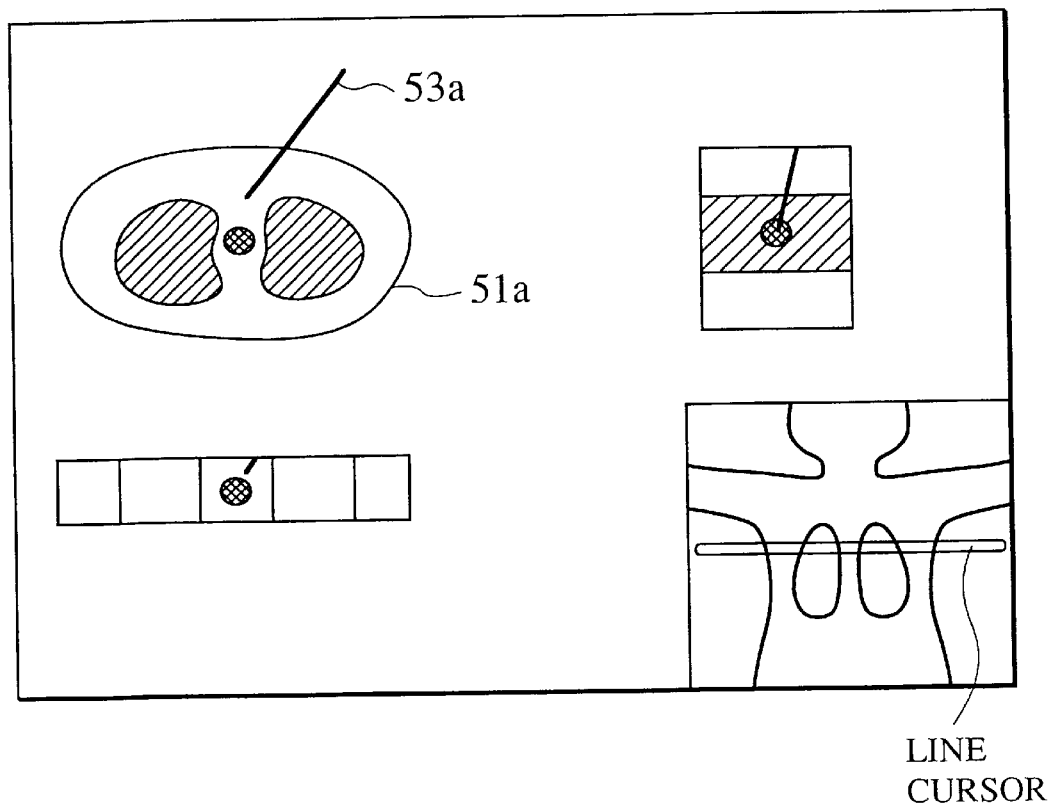
FIG. 23 is a view for showing one example of a screen image on which a display unit according to the fifth embodiment displays transmission data obtained by the photographing in FIG. 22, together with a tomographic image.

FIG. 23 shows an example of a display image output by the display unit 47b of the fifth embodiment.

The display unit 47b displays the image-reconstructed tomographic image, as well as the display data extracted by the transmission data extraction unit 33b. As the image as shown in FIG. 23 is outputted, it is possible to observe in real time the proceeding direction of the insertion object 53, from three directions. In other words, It is easily possible to display an image like a three-dimensional image from three directions. Note that when the image of the insertion object photographed in scanogram is further displayed together with a line cursor for displaying a scanning position, for example, on the screen, as shown in the right lower part in FIG. 23, it is further possible to understand the corresponding positions of the tomographic image and transmission data inside the subject displayed.

Conventionally, for obtaining an image of three-dimensional information as shown in FIG. 23, at first, an image of each slice is reconstructed from volume data acquired, thereby to prepare three-dimensional voxel data. Based on this voxel data, a display image as observed from three directions is prepared and then displayed. Therefore, this image reconstruction processing has required many hours, and it has also been difficult to real-time display a part including the Insertion object from a plurality of directions (for example, three planes)

On the other hand, according to the fifth embodiment, the image reconstruction unit 45 prepares a plane image from the transmission date extracted by the transmission data extraction unit 33b. The display unit 47b displays the prepared image together with the tomographic image. Therefore, it is possible to display an easy three-dimensional image in real time, so that the operator can carry out the operation accurately and promptly.

Sixth Embodiment

Next, an X-ray computerized tomography apparatus according to a sixth embodiment of the present invention will be explained in detail with reference to FIG. 24 and FIG. 25. In the above-described first and second embodiments, a range in which an image is to be reconstructed or a range in which an image is to be visualized is determined based on a position of an object detected by the object position detection unit 31. On the other hand, in the sixth embodiment, the movement of the gantry or the couch is controlled so as to scan only a necessary range of the subject, based on the position data of the object.

In other words, the sixth embodiment provides a function of automatically scanning a target organ inside the subject to be scanned, by automatically detecting the position of the target organ.

FIG. 24 is a block diagram for showing a configuration of the X-ray computerized tomography apparatus according to the sixth embodiment. The X-ray computerized tomography apparatus according to the sixth embodiment is a modification of the first embodiment shown in FIG. 3 in which a scan position determining unit 49 is added to the configuration of the first embodiment. Other configurations of the sixth embodiment are similar to those of the above-described embodiment.

The object position detection unit 31 of the sixth embodiment recognizes a shape of an arbitrary organ inside the subject by using the shape recognizing technique explained in the first embodiment. For example, a shape of a predetermined part such as a lung, a liver or a head, for example, is stored in advance. By matching this shape with the transmission data obtained by scanning, it is possible to recognize the target organ. The object position detection unit 31 outputs the position data of the organ obtained to the scan position determining unit 49.

The scan position determining unit 49 determines a scanning range necessary for photographing the organ, based on the position data inputted from the object position detection unit 31. The scan position determining unit 49 outputs the data indicating this scanning range to the system controlling unit 11. The system controlling unit 11 generates a scan position control signal for scanning a range in which the target organ exists, and outputs this scan position control signal to the gantry/couch controlling unit 13. The gantry/couch controlling unit 13 controls the movement of the couch or gantry, based on this scan position control signal.

FIG. 25 shows a procedure of the operation carried out by the operator when an organ is to be photographed by using the sixth embodiment.

At first, the operator lays a patient on the couch (step S61). Next, the operator inputs an instruction of a target portion (organ) of a subject to be photographed, by depressing a photographing part selection button, for example (step S62). When the instruction designating the part to be photographed has been input, according to the sixth embodiment, at first, the scanogram of the subject or the transmission data at a prescribed tube position acquired by the plane detector is acquired automatically. With the acquired transmission data used as an input, the object position detection unit 31 automatically detects a position of the target organ by using the shape pattern of the organ of the part designated by the operator (step S63). Based on the detected position data of the organ, the scan position determining unit 49 controls the scanning position of the target organ inside the subject to be photographed, through the system controlling unit 11, and then the transmission data of the slice including this target organ is collected in next scanning (step S64).

According to the sixth embodiment, the following effects can be obtained. When the operator has inputted an instruction designating the target part (organ) inside the subject, the X-ray computerized tomography apparatus according to the sixth embodiment at first automatically photographs a scanogram of the subject or the like and then detects the position of the target organ by using the shape recognition, according to the image data of the scanogram. Based on the detected position of the organ, the X-ray computerized tomography apparatus according to the sixth embodiment further scans only the range including this organ. Therefore, the apparatus can automatically photograph the target organ (part), without requiring a decision of the operator.

The first to the sixth embodiments can be structured by suitably combining them, in addition to the above-described configurations.

In summary, according to the above-described embodiments, it is possible to detect easily and in real time a position of an object such as an insertion object or an organ, based on the transmission data acquired, without involving an image reconstruction. Therefore, it is possible to acquire or display in real time the slice in which a desired object exists, after the acquisition of the transmission data. Accordingly, an accurate and prompt navigation of an operation can be achieved.

Further, by controlling the slice position so that X-rays are irradiated onto only the necessary slices at the next is scanning, based on the position data detected, it is possible to decrease unnecessary exposure of the subject to X-rays.

Furthermore, it is possible to substantially decrease the time required for photographing the target organ inside the subject, as well as it is possible to substantially improve the efficiency of the operation of the photographing.

It is to be noted that, besides those already mentioned above, many modifications and variations of the above embodiments may be made without departing from the novel and advantageous features of the present invention. Accordingly all such modifications and variations are intended to be included within the scope of the appended claims.

What is claimed is:

1. An X-ray computerized tomography apparatus comprising:
    an X-ray detection unit for detecting transmission X-rays from a plurality of directions irradiated from an X-ray beam generation source and transmitted through a subject;
    a data acquisition unit for acquiring transmission data according to the transmission X-rays detected by the X-ray detection unit:
    an object position detection unit for detecting a position of an object inside the subject, according to a part of the transmission data acquired by the data acquisition unit;
    a reconstructing range determining unit for determining a slice to be Image-reconstructed, according to the position detected by the object position detection unit; and
    an image reconstruction unit for reconstructing a tomographic image of a slice in which the object exists, according to transmission data acquired by the data acquisition unit, the transmission data being acquired in the slice determined by the reconstruction range determining unit.

2. The X-ray computerized tomography apparatus according to claim 1, wherein
    the object position detection unit includes: a transmission data extraction unit for extracting transmission data at a predetermined tube position of the X-ray beam generation source, for each slice, from the transmission data acquired by the data acquisition unit,
    whereby to detect a position of the object according to the extracted transmission data.

3. The X-ray computerized tomography apparatus according to claim 1, wherein
    the object position detection unit detects a position of the object by deciding a presence of the object by using a predetermined threshold of an X-ray absorption value.

4. The X-ray computerized tomography apparatus according to claim 3, wherein
    when the object is an insertion object, and when the transmission data within the threshold for showing a tip of the insertion object exists in the slice displayed previously, the object position detection unit decides whether or not there is the transmission data within the threshold in an adjacent slice in a positive proceeding direction of the insertion object, and
    when there is no transmission data within the threshold in the slice displayed previously, the object position detection unit decides whether or not there is the transmission data within the threshold in an adjacent slice in a negative proceeding direction of the insertion object, so as to detect the tip of the insertion object in correspondence with the proceeding direction of the insertion object.

5. The X-ray computerized tomography apparatus according to claim 1, wherein
the object position detection unit detects a position of the object by deciding a presence of the object by using a shape recognition.

6. The X-ray computerized tomography apparatus according to claim 1, wherein
the object position detection unit detects a position of the object according to transmission data of a plurality of slices acquired by the data acquisition unit.

7. The X-ray computerized tomography apparatus according to claim 6, wherein
the transmission data of the plurality of slices is obtained by scanning at a plurality of positions of a couch or a gantry, or by volume scanning using a two-dimensional detector having detecting elements laid out by a plurality of rows in a slice direction.

8. The X-ray computerized tomography apparatus according to claim 2, further comprising:
a tube position determining unit for determining the predetermined tube position of the X-ray beam generation source, based on the transmission data of a plurality of slices from a plurality of directions acquired by the data acquisition unit, and for sending data indicating a determined tube position to the transmission data extraction unit.

9. The X-ray computerized tomography apparatus according to claim 8, wherein
when the object is an insertion object, the tube position determining unit sets a tube position where the insertion object has the largest length on the transmission data from among the tube positions of a plurality of directions, as the tube position.

10. The X-ray computerized tomography apparatus according to claim 1, further comprising:
a display unit for visualizing the tomographic image reconstructed by the image reconstruction unit.

11. The X-ray computerized tomography apparatus according to claim 10, wherein
when the object is an insertion object, the display unit visualizes the tomographic image of the subject in a slice in which the tip of the insertion object exists.

12. The X-ray computerized tomography apparatus according to claim 10, wherein
when the object is an insertion object, the display unit forms a stacked display image of an image in a slice in which an object previously designated exists and an image in a slice in which the tip of the insertion object exists.

13. The X-ray computerized tomography apparatus according to claim 11, further comprising:
an operation controlling unit for instructing the X-ray detection unit and the data acquisition unit to acquire transmission data so as to make these units detect a position of the tip of an insertion object, based on an input by an operator, when the tip of the insertion object has deviated from an image displayed by the display unit.

14. The X-ray computerized tomography apparatus according to claim 11, wherein
the display unit always displays a tomographic image of the subject in a slice in which the tip of the insertion object exists, according to a position of the insertion object detected by the object position detecting unit.

15. An X-ray computerized tomography apparatus, comprising:
an X-ray detection unit for detecting transmission X-rays from a plurality of directions irradiated from an X-ray beam generation source and transmitted through a subject;
a data acquisition unit for acquiring transmission data according to the transmission X-rays detected by the X-ray detection unit;
an object position detection unit for detecting a position of an object inside the subject, according to a part of the transmission data acquired by the data acquisition unit;
a visualizing-range detection unit for determining a slice in which an image should be visualized, according to the position detected by the object position detection unit;
an image reconstruction unit for reconstructing a tomographic image, according to the transmission data acquired by the data acquisition unit; and
a display unit for visualizing the tomographic image of a slice determined by the visualizing-range detection unit.

16. An X-ray computerized tomography apparatus, comprising:
an X-ray detection unit for detecting transmission X-rays from a plurality of directions irradiated from an X-ray beam generation source and transmitted through a subject;
a data acquisition unit for acquiring transmission data according to the transmission X-rays detected by the X-ray detection unit;
an object position detection unit for detecting a position of an object inside the subject, according to a part of the transmission data acquired by the data acquisition unit; and
a scanning range determining unit for determining a range in which the subject is to be scanned, according to the position detected by the object position detection unit.

17. The X-ray computerized tomography apparatus according to claim 16, further comprising:
a position controlling unit for controlling a position of a couch or a gantry according to a range to be scanned determined by the scanning range determining unit.

18. The X-ray computerized tomography apparatus according to claim 16, further comprising:
an X-ray collimator provided between the X-ray source and a subject, and having at least one X-ray shielding plate moving along a slice direction; and
a collimator controlling unit for controlling a width of the X-ray shielding plate of the X-ray collimator, according to the range to be scanned determined by the scanning range determining unit.

19. The X-ray computerized tomography apparatus according to claim 16, wherein
the object position detection unit includes:
a transmission data extraction unit for extracting transmission data at a predetermined tube position of the X-ray beam generation source, for each slice, from the transmission data acquired by the data acquisition unit,
whereby to detect a position of the target object according to the extracted transmission data.

20. The X-ray computerized tomography apparatus according to claim 16, wherein
the object position detection unit detects a position of the object by deciding a presence of the object by using a predetermined threshold of an X-ray absorption value.

21. The X-ray computerized tomography apparatus according to claim 20, wherein when the object is an insertion object, and when the transmission data within the threshold for showing the tip of the insertion object exists in the slice displayed previously, the object position detection unit decides whether or not there is the transmission data within the threshold in an adjacent slice in a positive proceeding direction of the insertion object, and when there is no transmission data within the threshold in the slice displayed previously, the object position detection unit decides whether or not there is the transmission data within the threshold in an adjacent slice in a negative proceeding direction of the insertion object, so as to detect the tip of the insertion object in correspondence with the proceeding direction of the insertion object.

22. The X-ray computerized tomography apparatus according to claim 16, wherein the object position detection unit detects a position of the object by deciding a presence of the object by using a shape recognition.

23. The X-ray computerized tomography apparatus according to claim 16, wherein the object position detection unit detects a position of the object according to transmission data of a plurality of slices acquired by the data acquisition unit.

24. The X-ray computerized tomography apparatus according to claim 23, wherein the transmission data of the plurality of slices is obtained by scanning at a plurality of positions of a couch or a gantry, or by volume scanning using a two-dimensional detector having detecting elements laid out by a plurality of rows in a slice direction.

25. The X-ray computerized tomography apparatus according to claim 17, further comprising:

a tube position determining unit for determining the predetermined tube position of the X-ray beam generation source, based on the transmission data of a plurality of slices from a plurality of directions acquired by the data acquisition unit, and for sending data indicating a determined tube position to the transmission data extraction unit.

26. The X-ray computerized tomography apparatus according to claim 25, wherein when the object is an insertion object, the tube position determining unit sets a tube position where the insertion object has the largest length on the transmission data from among the tube positions of a plurality of directions, as the tube position.

27. The X-ray computerized tomography apparatus according to claim 16, further comprising:

a display unit for visualizing the tomographic image reconstructed by the image reconstruction unit.

28. The X-ray computerized tomography apparatus according to claim 27, wherein when the object is an insertion object, the display unit visualizes the tomographic image of the subject in a slice in which the tip of the insertion object exists.

29. The X-ray computerized tomography apparatus according to claim 27, wherein when the object is an insertion object, the display unit forms a stacked display image of an image in a slice in which an object previously designated exists and an image in a slice in which the tip of the insertion object exists.

30. The X-ray computerized tomography apparatus according to claim 28, further comprising:

an operation controlling unit for instructing the X-ray detection unit and the data acquisition unit to acquire transmission data so as to make these units detect a position of the tip of an insertion object, based on an input by an operator, when the tip of the insertion object has deviated from an image displayed by the display unit.

31. The X-ray computerized tomography apparatus according to claim 27, wherein the display unit always displays a tomographic image of the subject in a slice in which the tip of the insertion object exists, according to a position of the insertion object detected by the object position detecting unit.

32. The X-ray computerized tomography apparatus according to claim 16, further comprising:

a scan controlling unit for controlling the scanning of the subject in a scanning range determined by the scanning range determining unit, in correspondence with an input by an operator with respect to a portion inside the subject to be photographed.

33. An X-ray computerized tomography apparatus, comprising:

an X-ray detection unit having detecting elements laid out in a plurality of rows in a slice direction, for detecting transmission X-rays from a plurality of directions irradiated from an X-ray beam generation source and transmitted through a subject;

a data acquisition unit for collecting transmission data according to the transmission X-rays detected by the X-ray detection unit;

an image reconstruction unit for reconstructing a tomographic image of a slice in which an object inside the subject exists, according to the transmission data acquired by the data acquisition unit; and a display unit for displaying an image of transmission data at a predetermined tube position of the X-ray beam generation source from among the transmission data acquired by the data acquisition unit, together with the tomographic image reconstructed by the image reconstruction unit.

34. The X-ray computerized tomography apparatus according to claim 33, further comprising:

a data selection unit for selecting transmission data at a plurality of predetermined tube positions, based on the transmission data acquired by the data acquisition unit;

wherein the display unit displays the transmission data at a plurality of predetermined tube positions selected by the data selection unit, together with the transmission data reconstructed by the image reconstruction unit.

35. An X-ray computerized tomography apparatus, comprising:

an X-ray detection unit having detecting elements laid out in a plurality of rows in a slice direction, for detecting transmission X-rays for a plurality of slices from a plurality of directions irradiated from an X-ray beam generation source and transmitted through a subject;

a data acquisition unit for acquiring transmission data according to the transmission X-rays detected by the X-ray detection unit;

an object position detection unit for detecting a position of an object inside the subject, according to transmission data at a predetermined tube position of the X-ray beam generation source out of the transmission data for a plurality of slices acquired by the data acquisition unit;

a visualizing-range detection unit for determining a slice in which an image should be visualized, according to the position detected by the object position detection unit;

an image reconstruction unit for reconstructing a tomographic image, according to the transmission data acquired by the data acquisition unit; and a display unit for visualizing the tomographic image of a slice determined by the visualizing-range detection unit.

36. An X-ray computerized tomography apparatus, comprising:
a scan unit for scanning a subject to obtain projection data of the subject;
an object position detection unit, configured to said scan unit, for detecting a position of an object inside the subject, according to at least a part of the projection data; and
an image reconstruction unit, configured to said object position detection unit, for reconstructing at least one of a plurality of tomographic images in which the object is included according to the position.

37. An X-ray computerized tomography apparatus, comprising:
a scan unit for scanning a subject to obtain projection data of the subject;
an object position detection unit, configured to said scan unit, for detecting a position of an object inside the subject, according to at least a part of the projection data; and
a scan range determining unit, configured to said object position detection unit, for determining a range in which the subject is to be scanned, according to the position.

38. The X-ray computerized tomography apparatus according to claim 1, further comprising:
a visualizing range detection unit for determining a slice in which an image should be visualized, according to the position detected by the object position detection unit and a display unit for visualizing the tomographic image of a slice determined by the visualizing-range detection unit.

39. The X-ray computerized tomography apparatus according to claim 1, further comprising:
a display unit for displaying an image of transmission data at a predetermined tube position of the X-ray beam generation source from among the transmission data acquired by the data acquisition unit, together with the tomographic image reconstructed by the image reconstruction unit.

40. The X-ray computerized tomography apparatus according to claim 39, further comprising:
a data selection unit for selecting transmission data at a plurality of predetermined tube positions, based on the transmission data acquired by the data acquisition unit wherein the display unit displays the transmission data at a plurality of predetermined tube positions selected by the data selection unit, together with the transmission data reconstructed by the image reconstruction unit.

41. The X-ray computerized tomography apparatus according to claim 1, further comprising:
a visualizing-range detection unit for determining a slice in which an image should be visualized, according to the position detected by the object position detection unit; and
a display unit for visualizing the tomographic image of a slice determined by the visualizing-range detection unit,
wherein said object position detection unit detects a position of an object inside the subject, according to transmission data at a predetermined tube position of the X-ray beam generation source out of the transmission data for a plurality of slices acquired by the data acquisition unit.

42. An X-ray computerized tomography apparatus, comprising:
a scan unit configured to scan a subject to obtain projection data of the subject;
an object position detection unit configured to detect a position of an object inside the subject, according to at least a part of the projection data; and
an image reconstruction unit configured to reconstruct at least one of a plurality of tomographic images in which the object is included according to the position.

43. An X-ray computerized tomography apparatus, comprising:
a scan unit configured to scan a subject to obtain projection data of the subject;
an object position detection configured to detect a position of an object inside the subject, according to at least a part of the projection data; and
a scan range determining unit configured to determine a range in which the subject is to be scanned, according to the position.

44. The X-ray computerized tomography apparatus according to claim 1, further comprising:
a visualizing-range detection unit configured to determine a slice in which an image should be visualized, according to the position detected by the object position detection unit and a display unit configured to visualize the tomographic image of a slice determined by the visualizing-range detection unit.

45. The X-ray computerized tomography apparatus according to claim 1, further comprising:
a display unit configured to display an image of transmission data at a predetermined tube position of the X-ray beam generation source from among the transmission data acquired by the data acquisition unit, together with the tomographic image reconstructed by the image reconstruction unit.

46. The X-ray computerized tomography apparatus according to claim 39, further comprising:
a data selection unit configured to detect transmission data at a plurality of predetermined tube positions, based on the transmission data acquired by the data acquisition unit wherein the display unit displays the transmission data at a plurality of predetermined tube positions selected by the data selection unit, together with the transmission data reconstructed by the image reconstruction unit.

47. The X-ray computerized tomography apparatus according to claim 1, further comprising:
a visualizing-range detection unit configured to determine a slice in which an image should be visualized, according to the position detected, by the object position detection unit; and
a display unit configured to visualize the tomographic image of a slice determined by the visualizing-range detection unit,
wherein said object position detection unit detects a position of an object inside the subject, according to transmission data at a predetermined tube position of the X-ray beam generation source out of the transmission data for a plurality of slices acquired by the data acquisition unit.

* * * * *